United States Patent [19]
Jeffreys et al.

[11] Patent Number: 5,843,647
[45] Date of Patent: Dec. 1, 1998

[54] SIMPLE TANDEM REPEATS

[75] Inventors: Alec John Jeffreys, Leicester; John Armour, Leicestershire, both of England

[73] Assignee: University of Leicester, Leicester, England

[21] Appl. No.: 332,766

[22] Filed: Nov. 1, 1994

[30] Foreign Application Priority Data

Dec. 21, 1993 [GB] United Kingdom ............... 9326052

[51] Int. Cl.$^6$ ............... C12Q 1/68; C07H 21/02; C07H 21/04
[52] U.S. Cl. ............... 435/6; 536/23.1; 536/24.3
[58] Field of Search ............... 536/22.1, 24.3, 536/24.31

[56] References Cited

U.S. PATENT DOCUMENTS

| | | | |
|---|---|---|---|
| 4,683,202 | 7/1987 | Mullis | 435/91 |
| 5,075,217 | 12/1991 | Weber | 435/6 |

FOREIGN PATENT DOCUMENTS

| | | |
|---|---|---|
| 2 680 520 | 2/1993 | France . |
| 92/12262 | 7/1992 | WIPO . |
| 92/13101 | 8/1992 | WIPO . |
| 92/13969 | 8/1992 | WIPO . |
| 92/21693 | 12/1992 | WIPO . |
| 94/03640 | 2/1994 | WIPO . |

OTHER PUBLICATIONS

Edwards et al., DNA Typing and Genetic Mapping with Trimeric and Tetrameric Tandem Repeats, American Journal of Human Genetics, 1991, pp. 746–756.

Armour et al., Isolation of Human Simple Repeat Loci By Hybridization Selection, Human Molecular Genetics, Apr. 1994, pp. 599–605.

Armour et al., Isolation of Human Minisatellite Loci Detected By Synthetic Tandem Repeat Probes: Direct Comparison With Cloned DNA Fingerprinting Probes, Human Molecular Genetics, 1992, pp. pp. 319–323.

Karagyozov et al., Construction Of Random Small–Insert Genomic Libraries Highly Enriched For Simple Sequence Repeats, Nucleic Acids Research, 1993, pp. 3911–3912.

*Primary Examiner*—Stephanie W. Zitomer
*Assistant Examiner*—Ethan Whisenaut
*Attorney, Agent, or Firm*—Cushman Darby & Cushman Intellectual Property Group Of Pillsbury Madison & Sutro, LLP

[57] ABSTRACT

The present invention concerns a method for the identification from DNA of a fragment comprising a simple tandem repeat locus comprising the steps of:

i) contacting a DNA library with at least one hybridisation probe so as to identify a population of DNA fragments enriched for simple tandem repeats;

ii) isolating and cloning said population; and iii) screening of the resulting DNA library so as to identify an individual fragment comprising a simple tandem repeat locus.

Also provided are simple tandem repeats isolated by the method of the present invention, characterised in that they may be amplified at least in part by PCR using a specified pair of primers, together with amplification primers and probes specific to the simple tandem repeats so isolated.

The present invention also provides methods of genetic characterisation using the aforementioned simple tandem repeats, primers and probes.

18 Claims, 4 Drawing Sheets

SIMPLE TANDEM REPEATS

The present invention concerns methods for the identification from DNA, in particular from genomic DNA, of a fragment comprising a Simple Tandem Repeat (STR) locus, together with simple tandem repeat loci, primer sequences and hybridisation probes, as well as methods of genetic characterisation using the aforementioned simple tandem repeats, primers and probes.

Hybridisation techniques have been used in the past as preparative steps in the selection from cDNA libraries of sequences hybridising with cloned genomic DNA (see Parimoo, S., et al. (1991). *Proc. Nat. Acad. Sci. U.S.A.* 88: 9623–9627; and Lovett, M., et al. (1991). *Proc. Nat. Acad. Sci. U.S.A.* 88: 9628–9632) and in the isolation of (AC)n dinucleotide repeats from the mouse genome using immobilised short oligonucleotides as the hybridisation "target" (see Karagyasov, L., et al. (1993). *Nucleic Acids Res.* 21: 3911–3912). However, these techniques have various disadvantages, a primary disadvantage being that the use of short oligonucleotide "targets" results in hybridisation with a relatively restricted range sequences due to the inability of the "target" oligonucleotides to tolerate mismatches.

This inability to tolerate mismatches in the screening of libraries using relatively short oligonucleotides composed of perfect repeats (see, for example, Li, S.-H., et al. (1993). *Genomics* 16: 572–579) is further exemplified by the fact that loci containing frequently interspersed repeat unit variants may not be reliably detected. Interspersion of different repeat unit types is a common feature of many highly variable minisatellite loci, and has been exploited in the analysis of the mechanisms involved in the evolution of these longer repeat loci (see, for example, Armour, J. A. L., et al. (1993). *Human Mol. Genet.* 2: 1137–1145).

Hybridisation screening of unenriched genomic libraries in the past has been successfull in isolating simple tandem repeat loci from the human genome (see, for example, Weissenbach, J., et al. (1992). *Nature* 359: 79) but suffers from the general disadvantage of inefficiency; very large numbers of clones need to be screened from small-insert libraries for each positively hybridising clone, and large-insert (cosmid) clones require subsequent subcloning or other manipulation (see, for example, Edwards, A., et al. (1991). *Am. J Human Genet.* 49: 746–756; and Lagerstrom, M., et al. (1991). *PCR Meth Appl* 1: 111–119) to determine sequence immediately adjacent to the repeat block.

The present invention overcomes the aforesaid problems of the prior art and provides a simple and efficient method for the isolation of simple tandem repeat loci from DNA libraries and in particular from genomic DNA. This method is based upon prior enrichment for tandemly repeated DNA fragments, a prior enrichment which is sensitive to the presence of tandemly repeated DNA, but which is tolerant to the positioning of the tandem repeats and to mismatches. Only after enrichment by this method are the fragments cloned, resulting in a preselected library in which a significant proportion of clones comprise simple tandem repeats. This allows the rapid screening for and identification of usefully polymorphic loci by the simple examination and comparison of loci in different, possibly unrelated, individuals. Since the selected clones contain short inserts, the effort necessary to identify and sequence the region of the tandem array is also reduced. Additionally, the use of long tandemly repeated hybridisation targets in the present invention for hybridisation screening for minisatellite clones allows the isolation of relatively long arrays and tolerates mismatched variant repeat arrays, allowing the identification of a wide range of minisatellite clones, something which has been hitherto impossible to achieve.

In a first aspect of the present invention there is provided a method for the identification from DNA of a fragment comprising a simple tandem repeat locus comprising the steps of:
i) contacting a DNA library with at least one hybridisation probe so as to identify a population of DNA fragments enriched for simple tandem repeats;
ii) isolating and cloning said population; and
iii) screening of the resulting DNA library so as to identify an individual fragment comprising a simple tandem repeat locus.

The DNA library may be a genomic DNA library; the genomic DNA library may be any convenient population of DNA fragments such as human DNA, DNA from non-human species or subgenomic DNA libraries such as those generated by PCR from flow sorted chromosomes (see Telenius, H., et al. (1992). *Genomics* 13: 718–725). The genomic DNA library may be obtained by restriction digestion of genomic DNA.

The average fragment size within the DNA library may be less than 1.5 kilobases and may be less than about one kilobase. The fragment size may be from about 400 bp to about 1000 bp.

The hybridisation probe or set of probes may be immobilised on a solid phase such as a nylon membrane and may identify a particular class of simple tandem repeats. Such classes may include dimeric, trimeric, tetrameric, pentameric and hexameric tandem repeats such as trimeric or tetrameric repeats. Particular oligonucleotide probes for use in the present invention may include oligonucleotide probes comprising a tandemly repeated region of greater than 200 bp. The probe may comprise repeats having at least 70%, such as 80% or 90%, similarity to a given repeat sequence. The hybridisation probe may be a set of probes comprising mixed trimeric or tetrameric repeat DNA.

The population of DNA fragments enriched for simple tandem repeats may be amplified prior to cloning and this may be effected by PCR amplification. Universal linker sequences may be ligated to the ends of individual fragments, possibly prior to the enrichment procedure, and linker sequence specific primers may then be used to amplify the enriched population. Linker sequences may then be removed, for example by restriction digestion, prior to cloning.

According to the present invention there is also provided a method for the identification from genomic DNA of a fragment comprising a simple tandem repeat locus comprising the steps of:
i) ligating universal linker sequences to the ends of fragments comprised in a genomic DNA library so as to form a library for PCR amplification;
ii) contacting said PCR library with at least one hybridisation probe so as to identify a population of library fragments enriched for simple tandem repeats;
iii) separating and amplifying said population by PCR; and
iv) cloning and screening the resulting amplification products so as to isolate an individual fragment comprising a simple tandem repeat locus.

Cloning may be effected using any convenient cloning procedure and vector (for example pBluescriptII (Stratagene)) such as those described by Sambrook, J., Fritsch, E. F. and Maniatis, T. (1989). *Molecular Cloning A Laboratory Manual.* Cold Spring Harbor Laboratory Press.

Screening may be effected using any convenient hybridisation probe or set of probes comprising simple tandem repeat sequences. These may be the same as those disclosed above in respect of the enrichment procedure. Individual clones comprising simple tandem repeat loci may be analysed using conventional techniques to determine for example specific sequence information.

By "simple tandem repeat locus" is meant a tandemly repeated region having a periodicity of up to eight bases, for example up to six bases, such as up to five, four or three bases. Particular simple tandem repeat loci may have a periodicity of up to four or up to three bases.

The method of the present invention has been used to identify a number of simple tandem repeat loci as disclosed in Table 2, together with corresponding flanking primer sequences disclosed in Table 3 and hybridisation probes which specifically identify such loci.

Therefore, according to the present invention there are also provided simple tandem repeat loci for use in a method of treatment or diagnosis of the human or animal body characterised in that they may be amplified at least in part by PCR using any pair of primers as disclosed in Table 2.

The simple tandem repeats may comprise at least the sequence of at least any one of sequences 1–47. Where a pair of sequences are indicated (see Table 4 and sequences 1–47), the first part of the sequence may be separated from the second part of the sequence by an intervening sequence. This intervening sequence may comprise the repeat block of the simple tandem repeat.

The simple tandem repeats may be polymorphic. Many of the STR loci so identified have been shown to have unexpectedly high polymorphism. Therefore, they may have a heterozygosity of at least 80%; they may have a heterozygosity of at least 85%; they may have a heterozygosity of at least 90%.

The present invention also provides amplification primers specific to the aforesaid simple tandem repeats for use in a method of treatment or diagnosis of the human or animal body; the method of amplification may be PCR.

The present invention also provides probes specific to at least part of the aforesaid simple tandem repeats for use in a method of treatment or diagnosis of the human or animal body.

According to further aspects of the present invention there are also provided methods of genetic characterisation wherein sample DNA is characterised by reference to at least one of the aforesaid loci, primer sequences and probes. The method of genetic characterisation may comprise either the use of at least one hybridisation probe or it may comprise the use of polymerase chain reaction (PCR) primers specific to at least one of the aforementioned loci in order to amplify selectively the simple tandem repeat locus. The PCR primers may comprise at least one of the primers and probes of the present invention. The method of genetic characterisation may be used in genetic mapping studies such as linkage studies, and may be used in the genetic analysis and diagnosis of inherited or acquired disease alleles.

Such techniques of genetic characterisation may allow the generation of individual "identities" specific for one or more polymorphic loci, possibly those of the present invention. The generation of such individuals "identities" may be used to identify and characterise family relationships and may be used for e.g. forensic testing and in any technique which uses simple tandem repeats and their polymorphisms, such techniques possibly identifying, for example, inherited diseases and their causes.

Throughout the present application, the standard IUPAC nucleotide representation procedures are used. It should be noted that in these, R=A or G; Y=T or C; K=G or T; S=G or C; W=A or T; N=any base.

The invention will be further apparent from, but not limited to, the following description and examples with reference to the several accompanying figures and tables.

Of the figures.

Figure 1:
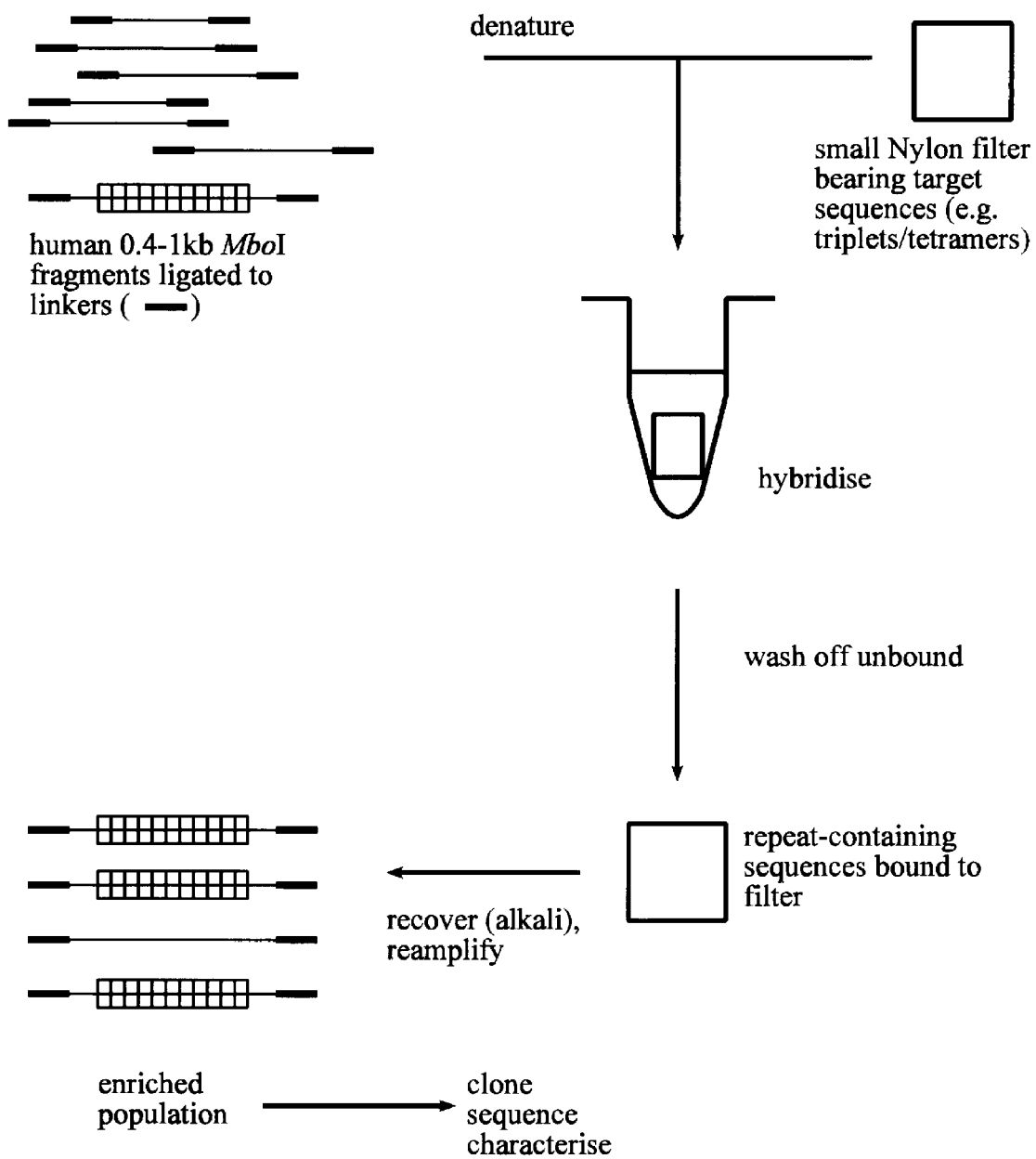
FIG. 1 shows a schematic summary of enrichment by filter hybridisation.

Of the Tables,

Table 1 shows characterisation by sequence analysis of 54 positively-hybridising clones from the repeat-enriched library, resulting in the first 24 polymorphic loci of Table 2

Table 2 shows properties of 24 polymorphic loci characterised in an initial study, together with thirteen subsequently identified loci. The number of alleles and heterozygosity levels shown were those observed in the analysis of 20 or more unrelated individuals from the CEPH pedigrees. EMBL is the European Molecular Biology Laboratory data bank; GDB is the Genome Database Table 3 shows PCR primer sequences and annealing temperatures for the polymorphic loci described; primers shown marked with an asterisk were end-labelled for genotyping on denaturing polyacrylamide gels.

Table 4 shows the simple tandem repeats and their sequence number or numbers. Where more than one number is given, the first part of the sequence may be separated from the second part of the sequence by an intervening sequence.

Results

During the characterisation of sequences isolated during an initial study (see Table 1), a total of 54 positively hybridising clones were analysed, giving 46 different sequences containing tandem repeat arrays (27 tetrameric; 19 triplet): These sequences were then used to design PCR primers (Table 1). Interestingly, two of these sequences showed near-perfect matches with sequences in the Genbank sequence database.

Of these sequences containing tandem repeat arrays, further characterisation revealed that 24 of them showed length polymorphisms when tested in 4 unrelated individuals. These polymorphic loci are shown in Table 2 together with 13 subsequently identified loci.

At these 37 new polymorphic loci, heterozygosity levels range from 9% to 95% (Table 2). The simplest factor useful in the prediction of variability was found to be the nature of the repeat block; tetramer repeat arrays not only showed more frequent polymorphism than triplets (18/27 v 6/19 in the initial study), but the average heterozygosity of those loci which were polymorphic was also higher (75% v 34% in the initial study). The locus represented by clone wglc3 contains a modestly variable triplet repeat (GGC)n array. However, the non repetitive region of the sequence determined shows 98% similarity over 148 bases with the published sequence of the human cDNA for translation initiation factor 4D (eIF4D) (see Smit-McBride, et al. (1989). *J Biol. Chem.* 264: 1578–1583). The region of near-identity begins abruptly at position 330 of wglc3, corresponding to position 22 of the eIF4D cDNA, and suggests that the fragment isolated in clone wglc3 may span an intron-exon boundary from the human eIF4D gene, and thus placing the (GGC)n repeat array within the preceding intron.

Although identified as containing tandem repeats by hybridisation, 5 of the 54 clones initially examined (about 10%) did not contain a recognisable tandem array. We assume that these clones might contain short imperfect arrays at some distance into the initial sequence analysis; where long (>8 repeat) arrays of near-perfect repeats were present they could easily be identified on sequencing autoradiographs, even when some distance into the clone. Alternatively, they might represent sequences rescued because of cross-hybridisation to a (non-repeated) part of one of the sequences contributing to the membrane-bound "target" DNA.

Hence the method of the present invention is a rapid and efficient method for isolating simple sequence loci, in this case exemplified by tri- and tetrameric repeat loci from the human genome.

Methods

The methods described below were used for the hybridisation selection of simple repeat loci, the characterisation of isolated sequences and the characterisation of these novel polymorphic simple sequence loci.

Hybridisation Selection of Simple Repeat Loci

FIG. 1 shows the general strategy for the hybridisation selection of simple repeat loci. More specifically, human MboI fragments (400–1000 bp) were ligated to (SAULA/SAULB) linkers to give a "whole-genome" PCR library (see Kinzler, K W. and Vogelstein, B. (1989). *Nucleic Acids Res.* 17: 3645–3653) from which tandem repeat-containing fragments were selected and reamplified. This population of molecules was denatured and incubated with two small nylon filters, one bearing mixed trimeric repeat DNA, the other bearing mixed tetrameric repeat arrays as described below. After hybridisation overnight at 65° C., fragments hybridising to each filter were recovered and reamplified using the linker primer SAULA. The reamplified fractions were compared with the input DNA by Southern blotting and probing with the pooled triplet or tetramer sequences used for selection, and were shown to be highly enriched for the respective sequences. Dot-blot analysis of serial dilutions showed that the enrichment was at least 50–100 fold.

Figure 2:
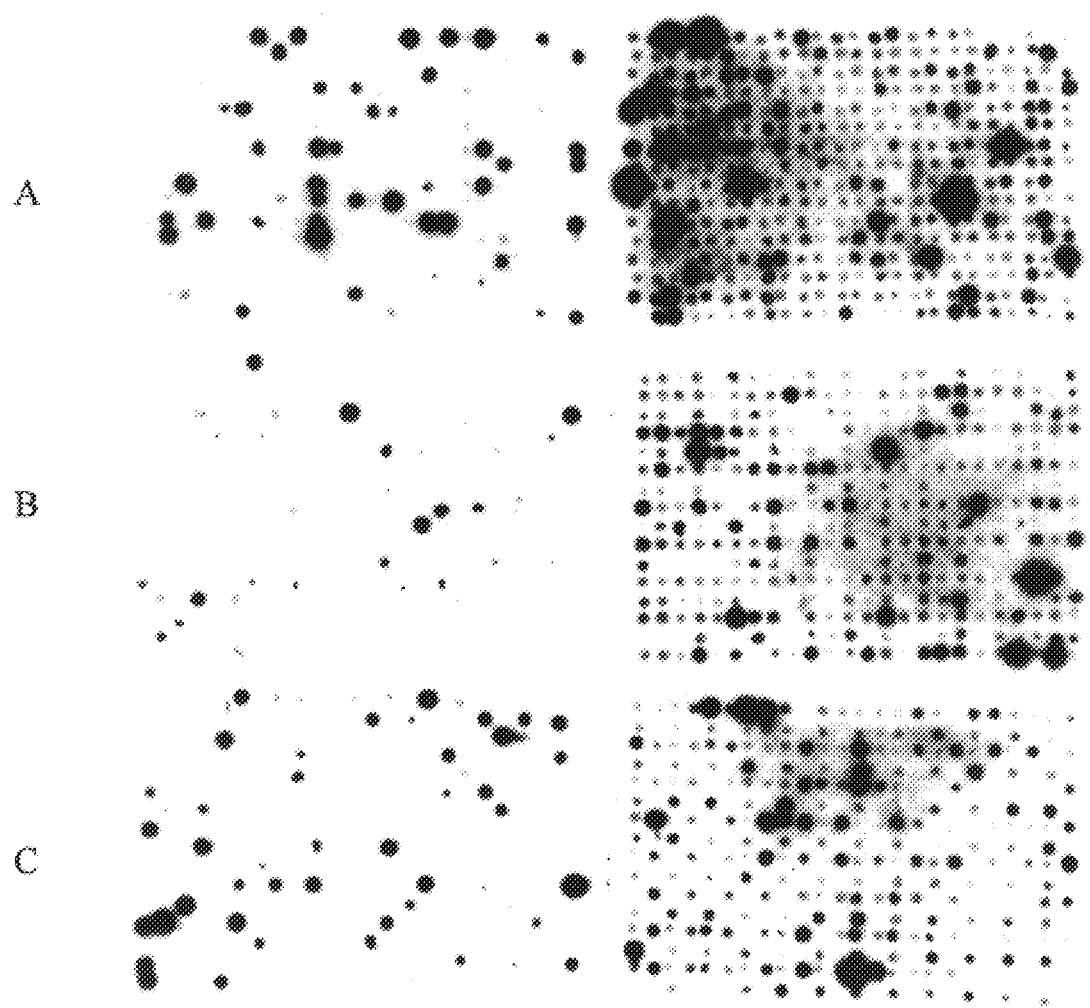
FIG. 2 shows an enrichment for tandem repeats after filter hybridisation. Three replicate filters (A, B and C) bearing DNA from over 1000 clones from an enriched library were screened by hybridisation using a mixed triplet probe (left panel) or mixed tetramers (right panel).

DNA fragments from the reamplified, enriched DNA fractions were digested with MboI (to remove linkers) and cloned into pBluescriptll vectors. Clones from the resulting library, containing both triplet and tetramer selected sequences, were picked into ordered array and screened by hybridisation to check the frequency of repeat-containing clones (see FIG. 2 for example). The probe mixtures originally used for filter hybridisation enrichment were also used as the hybridisation probes at this stage, and approximately 30% of clones initially studied gave positive hybridisation signals.

Characterisation of isolated sequences

The positively-hybridising clones were analysed for the initial characterisation of the enriched fragments. For each clone a first round of sequence analysis was performed using single stranded templates. In clones where the distal portion of unique sequence DNA could not be determined directly, further sequence information was derived, either from the other end of the insert (using double-stranded plasmid template) or by using a specific primer proximal to the array to extend the region already sequenced. Where a specific primer was used for sequence extension, this primer was subsequently used as an amplifier for PCR.

Novel polymorphic simple sequence loci

Figure 3:
FIG. 3 shows examples of genotyping at polymorphic tetranucleotide repeat arrays using $^{33}$P end-labelled primers and denaturing polyacrylamide gels; ten unrelated individuals were typed at wglcl2 (D7S822) and wglc4 (D8S580). Estimated fragment sizes (nt) are indicated.
Figure 4:
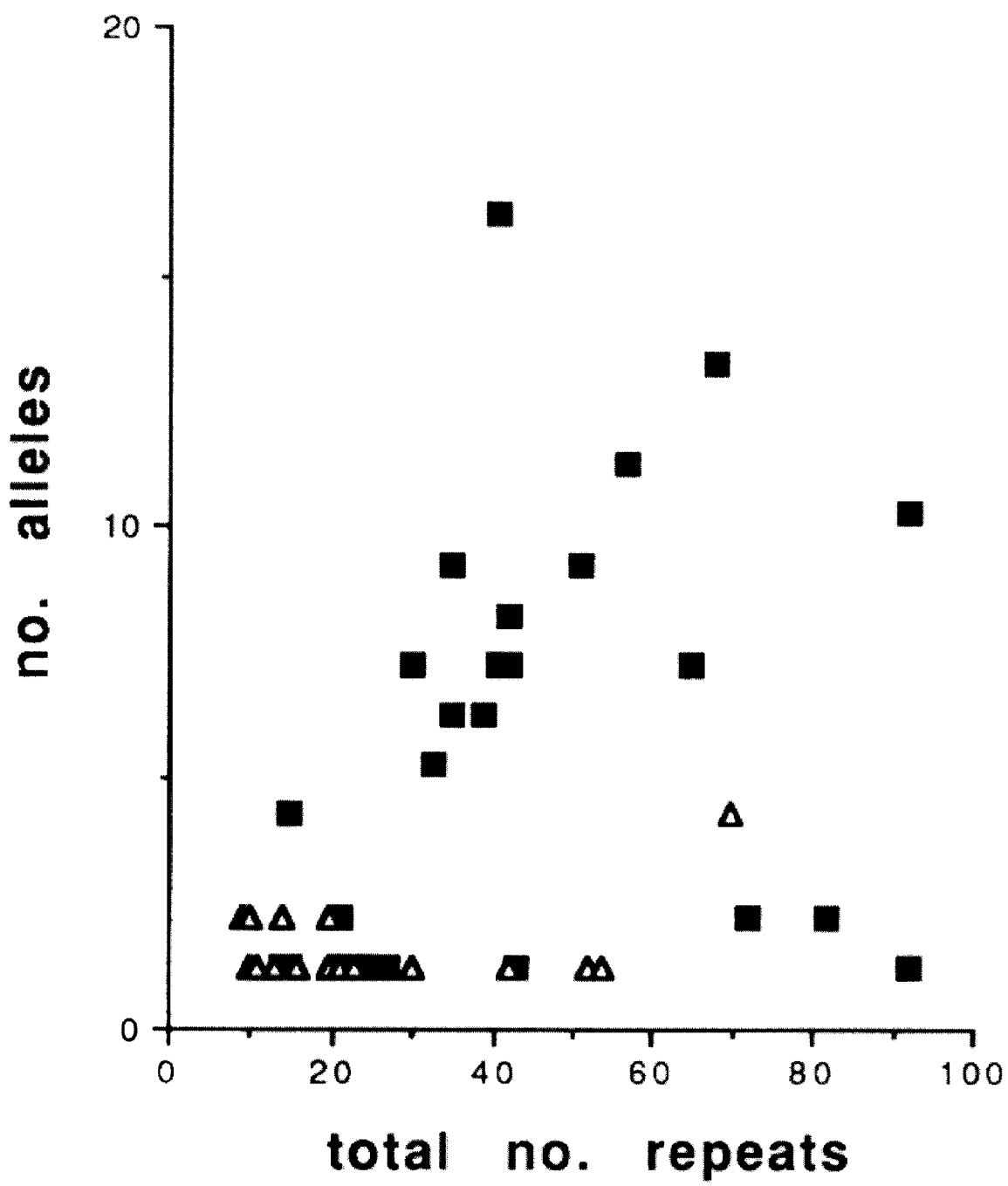
FIG. 4 shows the number of alleles observed at the 46 tandem arrays identified in Table 1 investigated shown plotted against total array length. Triangular symbols denote triplet repeat arrays and squares denote tetrameric arrays; loci found to be monomorphic (one allele only) have been included in the analysis.

Specific products were amplified by PCR from all of the 46 loci isolated. At most loci, specific amplification products could be satisfactorily resolved on agarose (NuSieve (RTM)) gels. At loci derived from expanded polyadenylate tracts, or where finer resolution was required, an end-labelled primer was used, and fragments resolved on denaturing polyacrylamide gels as described above; examples of tetranucleotide loci typed by this method are shown in FIG. 3. The polymorphic loci identified are shown in Table 2.

The loci have been initially mapped using a combination of somatic cell hybrid analysis and linkage in a small number of CEPH pedigrees as described for minisatellite loci (see Armour, J. A. L., et al. (1990). *Genomics* 8: 501–512; and Armour, J. A. L., et al. (1992). *Human Mol. Genet.* 1: 319–323. At many loci, the placement of recombinations could be inferred from linkage analysis, and thus a tentative interval containing the locus could be defined even from the analysis of only two or three pedigrees. These putative placements determined by linkage analysis (Table 2) were made using the NIH/CEPH maps of the human chromosomes (see NIH/CEPH Collaborative Mapping Group (1992). *Science* 258: 148–162) as a framework. In all cases a LOD score of 3 or more was required as evidence of linkage.

General methods

The following general methods were used in the hybridisation selection of simple tandem repeat loci and the characterisation of isolated sequences.

General PCR conditions

PCR was carried out using the buffer described by Jeffreys, A. J., et al. (1990). *Cell* 60: 473–485 and 0.05 U/$\mu$l Taq polymerase; unlabelled primers were added to a final concentration of 1 $\mu$M. Cycling conditions were: for the whole genome PCR library, 95° C. 1 min/67° C. 1 min/70° C. 2 min; for amplifying simple repeat loci using locus-specific primers, 95° C. 1 min/T° C. 1 min/70° C. 1 min; the annealing temperature T used for each polymorphic locus is shown in Table 3 (SEQ ID NO:52 through SEQ ID NO:125). These annealing temperatures gave good results in the PCR buffer used. In other buffer systems different temperatures may improve genotyping.

For amplification to levels visible after ethidium staining, 100 ng genomic DNA was amplified for 32 cycles. Amplified fragments were resolved by electrophoresis in NuSieve (RTM) gels (FMC BioProducts, 2.5–4.5% according to fragment size) in 0.5x TBE buffer, and DNA detected by ethidium staining. Loci derived from expanded (Alu) polyadenylate tracts were most clearly detected after end-labelling of the non-Alu PCR primer and autoradiography of dried polyacrylamide gels; at other loci polymorphism could be detected on ethidium stained agarose gels, but the use of polyacrylamide provided added resolution of closely-spaced alleles. One primer was end-labelled (1.5 pmol primer per subsequent PCR reaction) using [$\gamma$-$^{33}$P]ATP and T4-polynucleotide kinase. This labelled primer and 10 pmol unlabelled primer were then used with 0.05U/$\mu$l Taq polymerase in a 10$\mu$l PCR. Table 3 shows the primer used for end-labelling marked with an asterisk. In general, 18 cycles were sufficient to give clean typing from 100 ng genomic DNA; details of PCR conditions and primer sequences for the first 24 polymorphic loci can be found in GDB.

Whole genomic PCR library construction

SAU linkers were made by annealing equimolar amounts of SAULA (SEQ ID NO:48) (5'GCGGTACCCGGGAAGCTTGG3') and 5' phosphorylated SAULB (SEQ ID NO:49) (5'GATCCCAAGCTTCCCGGGTACCGC3') as described by Royle, N. J., et al. (1992). *Proc. R. Soc. Lond. B* 247: 57–61. Human genomic DNA pooled from 20 unrelated individuals was digested with MboI and a 400–1000 bp fraction size-selected after agarose gel electrophoresis. 200 ng of DNA from this fraction were ligated with 2μg SAU linkers, a linker:fragment molar ratio of about 250:1. After a further round of size-selection to remove linker dimers, the library was amplified using SAULA primer to give products in the 400–1000 bp range.

Tandem repeat "target" sequences

Both naturally occurring and synthetic sequences were used as target sequences in hybridisation selection. Where cloned or amplified loci were used as a source of tandemly repeated DNA, care was taken to use fragments which did not contain human dispersed repeat elements. The triplet repeat sequences ACC and AGG were selected using a DNA fragment from a cloned human locus, pMS633, containing about 2 kb of interspersed AGG/TGG(=ACC) repeats. Tandem arrays of the other triplet sequences used (AGC, ACG, ATG, AGT and CCG) were synthesised as follows: 18 mer oligonucleotides of each sequence and its complement were synthesised, phosphorylated, annealed and ligated into concatemers as described by Vergnaud, G. (1989). *Nucleic Acids Res.* 17: 7623–7630. Fragments larger than 200 bp were size-fractionated from the ligated DNA and subjected to cycles of PCR in the absence of primers to selectively lengthen tandem (rather than inverted) arrays (see Collick, A. and Jeffreys, A. J. (1990). *Nucleic Acids Res.* 18: 625–629), and fragments of apparent size greater than 1000 bp recovered from a 1% agarose gel. The triplet sequences AAT, AAG and AAC were not used in order to avoid heavy bias towards triplet repeats arising from retroposon tails (see Beckman, J. S. and Weber, J. L. (1992) *Genomics* 12: 627–631).

The self-complementary tetrameric repeat sequences CATG and CTAG were synthesised as 16mer oligonucleotides and assembled into long arrays by ligation and primer-free PCR. For other tetrameric sequences, cloned or amplified genomic fragments were used. DNA from the tetramer repeat locus composed of ATGG repeats near the human myelin basic protein gene (see Boylan, K B., et al. (1990). *Genomics* 6: 16–22) was amplified from human genomic DNA using the primers MBP1 (SEQ ID NO:50) (5'ACAAGGACCTCGTGAATTAC AATC3') and MBP2 (SEQ ID NO:51) (5'ACAGGATTCACTCACATATTCCTG3'), to give fragments of about 1 kb. DNA containing GGCA repeats was amplified from the mouse minisatellite clone p9.2 (see Gibbs, M., et al. (1993). *Genomics* 17: 121–128). A subcloned fragment from cosmid G2 (see Armour, J. et al. (1992). *Ann. Hum. Genet.* 56: 183) contains about 800 bp of interspersed ACCC and ATCC repeats; the human minisatellite clone pMS630 (see Armour, J. A. L., et al. (1992). *Human Mol. Genet.* 1: 319–323) contains the octameric repeat (GGAGGGAA) and was thus used to select AGGG and AAGG tetramer repeats.

Hybridisation Selection

DNA fractions containing the different trimeric arrays were pooled, denatured by treatment with alkali (KOH, final concentration 150 mM), neutralised by adding 0.25 volumes of IM TRIS-HCl pH 4.8, and a total of 1 μg spotted onto a small (3mm ×3mm) piece of nylon filter (Hybond-N$^{fp}$, Amersharn). When dry, the filter was exposed to ultraviolet light to bind the DNA. A similar small filter was made using the pooled tetrameric repeat fragments. Since the filters were to be used to select different types of sequence from the same input DNA, they could be used together in the same hybridisation. The filters were prehybridised in 1 ml phosphate/SDS buffer (see Church, G. M. and Gilbert, W. (1984). *Proc. Nat. Acad. Sci USA.* 81: 1991–1995) at 65° C. and transferred to 100 μl of the same buffer at 65° C. in an Eppendorf tube.

Input DNA was amplified from the whole genome PCR library and about 1 μg denatured with alkali, neutralised, and added to the buffer containing the filters; the reaction was covered with paraffin oil and incubated overnight at 65° C. The filters were washed thoroughly in 0.2×SSC, 0.01% SDS at 65° C. After washing, the DNA bound to each filter was removed by treatment (at room temperature) with 50 μl of 50 mM KOH/0.01% SDS, followed by 50 μl of 50 mM TRIS-HCl(pH7.5)/0.01% SDS; the washings from each filter were pooled, and recovered DNA ethanol precipitated using primer SAULA (final concentration 1 μM) as a carrier.

Hybridisation-selected DNA was reamplified, digested with Mbol and cloned into pBluescriptII vectors (Stratagene). Clones were picked into ordered array for ease of screening and clones replicated from microtitre plates onto Nylon filters in groups of four as described by Brownstein, B. H., et al. (1989). *Science* 244: 1348–1351

Sequence determination and analysis

DNA sequence was initially determined from clones hybridising positively with tandem repeat probes using dideoxynucleotide chain termination with T7 DNA polymerase (see Tabor, S. and Richardson, C. C. (1987). *Proc. Nat. Acad. Sci. USA.* 84: 4767–4771) on single stranded templates. Where this proved insufficient to determine sequence on both sides of a tandem array, additional sequence was determined either from the other end of the clone using double-stranded templates, or after extension of the sequence using a specific oligoncleotide primer; any specific primer used in sequence analysis was subsequently recruited as one of the amplifiers in PCR.

The sequence determined was analysed using the suite of programs developed at the University of Wisconsin (Genetics Computer Group (1991). Program Manual for the GCG Package. Version 7. April 1991. S75 Science Drive, Madison, Wis., USA 53711); updated sequence databases were searched using the BLAST (see Altschul, S.F., et al. (1990). *J. Biol.* 215: 403–410) network service at the NCBI.

It will be appreciated that it is not intended to limit the invention to the above example only, many variations, such as might readily occur to one skilled in the art, being possible, without departing from the scope thereof as defined by the appended claims.

DNA Sequence Information

SEQUENCE: 1, corresponds to wg0e7; Length 377 (SEQ ID NO: 1)

```
  5' GATCAAATTT ATTCTCTCCT TTGCACACTG GAAGTGCAAG TAACATTTCT
 51  TCCTTCTCCT GCTCCTCCTC CTGATAACAA TGGTGATGAT GATGGTGATG
101  ATGGTGGTGG TGATGGTGAT GTTGGTGGTG ATGATGGTGA TGGTGATGGT
151  GGTGATGATG GTGGTGGTGA TGGTGGTGGT GATGGTGGTG GTGATGGGGT
201  GGTGACGGTG ATGTTGACGG TGGTGGTGGT GGTGGTGATG GAGTGGTGAT
251  GGAGTGGTGA TGATGGTGGT GATGGTGGTG ATGGCGATAA CAAACATATA
301  TTAAGACCTT ACCATGGCTR GGCATGGTGG CTGATRCCTG TAATCCCAGC
351  ACTTTGGGAG GCCGAGGCGG GCAGATC
```
SEQUENCE: 2, corresponds to first part of wg1a2; Length 346 (SEQ ID NO: 2)

```
  5' GATCATTCGG AAGAAAGTGT GGAAGCAGCA GCAAAGAGTG GAAAATGAAA
 51  AGAGAAACTC TGGAGAAGGC AAGGTGGGCA GGAGCAGGAC TGTGCCGCCT
101  GCACCCATGC AGGCTAGGCG TTGTCCAACA CTGGGGCACC CGTCACTCAG
151  ATTGAGATGA GGGACAATGA GAGGAGCCTG GAGGAGAGCT CCACACAAAT
201  AAAGGGAGAA GCCTATGCAG GGGCTGGAGA TTCCTTCTGT GGTGACAGAG
251  CATGGCATAG TTAGATTCAC AGACTNNNNN NAGATCGAGA GAATGATGCG
301  TGCTCTTCTC ATCTCTCAAG CAGCAATGCA GGGGGAACAT CAGCTG
```
SEQUENCE: 3 corresponds to second part of wg1a2; Length 57 (SEQ ID NO: 3)

```
  5' TTGTTTTTTT GATGGAGTCT CACTCTGTTG CCCAGGCTGG AGTGCAGTGG
 51  CGTGATC
```
SEQUENCE: 4 corresponds to first part of wg1a3; Length 217 (SEQ ID NO: 4)

```
  5' GATCCATCCA TCCTTCCTCC CTCCTTCCCT CTCTTTCTAC CTCTTTCTCG
 51  CTCTCTCTTT CTTCCTTCCT TCCTCCCTCC CTCCCTCCTT CCCTCCCTCC
101  CTTCCTCCCG CCCTCCTTCC CTTTTCCCTT CCCCCTTCCT CTTTCTTTCT
151  CTTTCTTTCT CTTTCTTTCT TACTTTCTTT CTTTCTTTCT TTCTTTCTTT
201  CTTTCTTTCT TTCTTTC
```
SEQUENCE: 5 corresponds to the second part of wg1a3; Length 43 (SEQ ID NO: 5)

```
  5' GAGTCTCACT CTGTTGCCCA GGCTGGATTG CAGTGGCAGG ATC
```
SEQUENCE: 6 corresponds to wg1a9; Length 286 (SEQ ID NO: 6)

```
  5' GATCAGTTTC TGACTGCTGG GCGGGACAAA GCCTCCTGAA GTTGCTGCGA
 51  GGCACCTCCC CCTGTGAGCA GAGCTTGGTA CAGCCCAAAT AGTTTTCAGG
101  TTAAGAAAGC CAGAATCTTT GTTCAGCCAC ACTGACTGAA CAGACTTTTA
151  GTGGGGTTAC CTGGCTAACA GCAGCAGCGG CAACGGCAGC AGCAGCAGCA
201  GCAGCAGCAG CAGCAGCAGC AGGGCTCCTG GGATAACTCA GGTGAGTAGA
251  GAGGGAATTC GCAAACTTAC CCTGGAGTTT TATTTC
```
SEQUENCE: 7 corresponds to wg1c3; Length 457 (SEQ ID NO: 7)

```
  5' GATCCAATGG CTCTTTAGTC AGGGTGTTAT GTCCTGAAAA TAGGTGACAA
 51  CTGCAAACCA TCCTCTGGTG TCCAGAGACT TTAACAAGGT TTGTTTCACA
101  GAGACTGAGG GCAGAAAAAA GGAAATGGCC TAAAAAGGTG GGTTTGCTGT
151  GTTGCCTCAC ACTACTTGAT TCATGGTTCT GATTCTAAAA ATCTCACTTG
201  ATACTTGATT TCATATGAAA GACGTGTAAA ATGCCTGGGT AGAGGCGGCG
251  GCGGCGGCGG CGGCGGGCTC GGAGGCAGCG GTTGGGCTCG CGGCGAGCGG
301  ACGGGGTCGA GTCAGTGCCG TTTGCGCCGG TTGGAATCGA AGCCTCTTAA
351  AATGGCAGAT GATTTGGACT TCGAGACAGG AGATGCAGGG GCCTCAGCCA
401  CCTTCCCAAT GCAGTGCTCA GCATTACGTA AGAATGGCTT TGTGGTGCTT
451  AAAGGCT
```
SEQUENCE: 8 corresponds to wg1c4; Length 370 (SEQ ID NO: 8)

```
  5' GATCACACCA TTGCACTCCA GCTTGGGCAA CAGAGTGAGA CTCCATCTCA
 51  ACAAAAAAAA GAAAGAAAAG AAAAGAAAGA AAAGAAAAGA AAAGAAAAGA
101  AAGAGAAAGA AAGAGAAAAA GAAAGAAGGA AGGAAGGAAG GAAGGAAGGA
151  AGGAAGGAAG GAAGGGAGGA AGGAAGGAAG GAAAGCAAGA AAGAAAGAAA
201  GAAAGAAAGA AAGAGAAAGA AAGAAACTAT CCAAACCAAT CTGATAGAGC
251  TGAAAAACTT ACTACAAGAA TTTCATAATA CAATCAGAAG TATTAACAAC
301  AAAATGCACC AAGCTAAGGA AAGAATCTCA GAACTAGAAG ACCCAGTTCT
351  TTGAATCTAT TCAGACAGAC
```
SEQUENCE: 9 corresponds to wg1c5; Length 367 (SEQ ID NO: 9)

```
  5' GATCTCAATA AACATTGATA CTGGAGGGAT GAAATGAAGG AAGGATGGAT
 51  AGAAGGCTAT AAGGATGGGT GGATGGATAA ATGGATGGAT GGATGGATGG
101  ATGGATGGAT GGATGGATAG ATGGATGGAT GGAAAAATGG ATAGATGGAT
151  GGGTGGATGG ATGAATGGAT GGATGGATGG ATGGATGGAT GGATGGGTGG
201  ATGGATGAAT ATATTGGGTG GATGGATGGA AGGAAGGAAG GAAGGAAGGA
251  AGGAAGGAAG GAAGGAAGGA AGGATGGTAG AAGAAAGGTA GTACCAGTAT
301  GCTTTAGCTC ATGCAGGCAA ACAGATGATG GGCAGAGGGA AGCATGGTGG
351  CTGATTACAG GAGGATC
```
SEQUENCE: 10 corresponds to wg1d1; Length 434 (SEQ ID NO: 10)

```
  5' GATCCTCTTG CCTAGGCCTC CCAAAGTGCT GGGATTACAG GCAAGAGCCA
 51  CCACGTCCCG CCTCTAATTT CTCTCCTCTT CTCTCCTCTC CTTTCCTTTC
101  CTCTCCTCTC CTTTCCTTTC CTCTTCTCTT CTTGTTTTTT TCTTTTCTNC
151  CCTCCCTCCC TCCCTCCCTC CCTCCCTCCC TCCTTCCTTC CTTCCTTCCT
201  TCCTTCCTTC CTTCCTTCCT TCCTTCCTTT TTGAGACAGA GTTTTGTTCT
```

```
251 GTCACCCAGA CCTGAGTGCA ATGGGCACAA TTTTGGCTCA CTGCAACCTC
301 CATCTCCCCG GTTCAAGTGA TTCTTCTGCC TTAGCCTCCC GAATAGCTGG
351 AACTACAGGC ACCTGCCACC ATGCCCCAGC TAATTTTTTG TATTCTCAGT
401 AGAGATGGGG TTTACCATGT TGGCCAGGCT GCTC
        SEQUENCE: 11 corresponds to wg1d5; Length 325 (SEQ ID NO: 11)

5' GATCGCGCCA CTGTACTCCA GCCTGGGCGA CAGAGCGAGA CTCTGTCTAA
 51 AAAAAAAGAA AAAAGAAAAA AAAGAAAGAA TGAGAGAAAG AGAGAAGGAA
101 GGAAGGAAGG AAAAGGAAAG AGAGAGAGGA AGGAAGGAAG GAAGGAAGGA
151 AGGAAGGAAG GAAGGAAGGA AGGAAGGGAG GGAGGGAGGG AGGGAGGGAG
201 GGAGGGAGGG AGGGAAAGGC AGGGAGAAAG TTCTGGGAGC TAGGGAGTGC
251 CCGGGGTGGG GAGCTCCAAG AACAAGCCCC AGGGAGCTGT AACAAAGACT
301 TTGTCACAGC TAGCCTGAAG CTAGC
        SEQUENCE: 12 corresponds to wg1d6; Length 263 (SEQ ID NO: 12)

5' GATCCCACCT GCCATACGGT GGGATTTCTA GGACTATACA AATGACAGAA
 51 GGGTAGTAAG AGGAAGACTG TGTTGCTTAA TGAGGTTTCC AGAAATTGGT
101 AATGATATTT GTAATTCCAA ATCCTACTAC AAGGAACTGT GGCTACAATA
151 TTGATGCTGC TGCTGCTGCT GCTGCTAATT TGATGAAGTA GGCTAATCCG
201 CATGGCTACA TCTCTGTATT AGTCCATTCT CGCGCTGCTA TAAAGAAACT
251 ACCTGTGACT GGG
        SEQUENCE: 13 corresponds to wg1d10: Length 160 (SEQ ID NO: 13)

5' GATCCTGTTC ATGGTACAAA GCTTTCCCTA GCAGCCTGCC CTCCCTAGCC
 51 TGCTTACCTT GAGNNGAGAG GAAGCTGAAG TAGCAGCAGC AGCAGCAGCA
101 GCAGCAGAGT TNCCAGAAAG TGACCCCCTC CCCTGAACAC AGCAGGAAGC
151 AGCAGTCCAA
    SEQUENCE: 14 corresponds to the first part of wg1d11; Length 238 (SEQ ID NO: 14)

5' GATCATTTCA GTCTGCACAA GAATGCTTGG CCTTTTAATT CCAACTTCAC
 51 AGTTGAGAAA ACTGATACTC AAGGCAAAGA ATCTTCTCAG TAGTCAGAGT
101 CAATAACTGC AGGAACTAAG ACTGGAACCC AAGTTTTCTG CCTGGTATGT
151 TGGGCCTAGA AGGGAACTGC TATTCCTATC TCTCCATCTT TCCTTCCATC
201 TTTCCTTCCT TCCTTCCTTC CTTAATCCTT CCTTCCTT
    SEQUENCE: 15 corresponds to second part of wg1d11; Length 120 (SEQ ID NO: 15)

5' TTCCTCTCTC ACTGTCTCCC TCNCTCTCTG TCTCCCTCCT TCCTTTCTTC
 51 ACCTTCTTTC TACTTTTTTA AGAAACAAGG TCTGGCTTTG TCACCCAGGC
101 TGGAGTGCAG TGGCGTGATC
        SEQUENCE: 16 corresponds to wg1e1; Length 445 (SEQ ID NO: 16)

5' GATCTTGAGA CAGGGTCATC CTGGATTACT GGAGTGTGCC CTAAATCCAT
 51 TGACAAGTGT CCTTAGGAGA GACGCAGAGT GGAGGCACAC AGTGGGAGGA
101 CGAGGCCACT TGAAGACTGA GGCCGGGATT GCAGCGATGC AGCCACAACC
151 CAGGAAAGTC CGGGGCCACC AGCGGCTGGA AAAGGCAAGG GAGGGGTCTT
201 CTGGCTCTTC AACAATAAGA GAGTAAATTT CTGGTGTTTT AAGCCACCTG
251 GTTTGTGGTG CTTTTTCCTT CCCTCCTTCC TTCCTTCCTT CCTTCCTTCC
301 TTCCTTCCTT CCTTCCTTCC TTCCTTCCCT CCCTCCCTCC CTCCCTCTCT
351 CCCTCCCTCC CTCCCTTCCT TCCTCTTCTT TTTCTCTCCC TCTCTCCTTT
401 TTTTCTTTTT TTTGGTGGAG TCTTGCTGTG TCGCCCAGGC TGGAG
        SEQUENCE: 17 corresponds to wg1e4; Length 591 (SEQ ID NO: 17)

5' GATCCCAAAA TACTGGCCTC TCATAGTGAT AGATTTAAAA GATTGCTTCT
 51 TTACCATTCC TTTAGCTACC CAAGATTATG AAAAATTTGC TTTTACTGTT
101 CCTTCTATAA ATAACAAAGA ACCAGTGGAC AGATACCATT GGAAAGTACT
151 GCCACAAGGC ATGCTAAATA GCCCGACTAT TTGTCAAACT TATATCGGAA
201 AAGTTATGAA GCCAATTAAA GAACAATTTT ACAAATGTTA TATTATCCAT
251 TACATGGATA ATTTTATTTG CAGCTGAAAC TAAAGAGGAA TTAATGCTAT
301 GCTACAAACA ACTGGAAAAG GCTGTGACTG CAGCGGGATT AATCAATCAT
351 AGCCCTGATA AAATCCAAAC TTCTACTCCC TTTCAGTATT TAGGAATGAA
401 AGCAGAATAA AGTACTATCA AGCTTCAAAA GGTTCAAATT AGAAGAGATG
451 ATTTAAAAAC TCTAAATGGC CGGCCTGCCT TCCTTCCTTC CCTCCCTCCC
501 TCCCTCCCTC CCTCCCTTCC TTCCTTCCTC CCTCCCTCTC TCTTTCGACG
551 GTCTCCCTCT GTTGCCGAGG CTGGACTGTA CTGCCATGAT C
        SEQUENCE: 18 corresponds to wg1e7; Length 485 (SEQ ID NO: 18)

5' GATCACTTGA GGCCAGGAGT TCAAGACCAG CCTGAGCAAC CTAGTGAAAC
 51 CCCGTTTCTA CAAAAATAA AAATTTAAGA AATAGCTGGA TGCAGAGGCA
101 TCTGCCTGTA GTCCCAGCTA CCCAGGAGGT TGAGGAAGGA GAATCACTTG
151 AGCCCAGAAG CTTGAGGTTG TAGTAAGGAA TGTTCATGCC ACTGCACTGC
201 AACATGGGTG ACAGTGCAAG TTTCTGCCTC AAAAGGAAGG AAGGAAGGAA
251 GGAAGGAAGG AAGGAAGGAA GGAAGGAAGG AAGGCAGGCA AGAAGAAAAG
301 AAGGCAGGGA GAGACGGAGG GAAAGACAGA AAAGAAAGAA AACCTATAAA
351 AAAGTATAAT CCTGTGAGTC CACAGATGAG ACAGAGAAAA ATCTGGAAAG
401 GATTTTAAAA TAAGTATGCT TAAATTCTTC AAAGAGACAT AGAAAGGAAT
451 AGAACCCACA AAATAAGAAT GGAAATATTC GAAAA
        SEQUENCE: 19 corresponds to wg1e12; Length 597 (SEQ ID NO: 19)

5' GATCTTATGA CATTTTCCCA GGACACCAAG ATATAAAACC CCAACCAACA
 51 TTGCTACTGC TAAAGTAAAC TTTTGCCTGG CTTGCCAAGA TTTTTGGCCA
```

-continued

```
101 AGAAATGAGA TTTCCTGAGG GTGGCATTCC CTCTGCACTA CCAAAGTCTC
151 CTTCTGAGAC TTTTTGGTCA GCTTATGAAG CTTCTCAAGG CAAGTGTCTG
201 GTTAGCATCT CCCTCCCTCC ACTCTGGAAA TCTTAAAGCT GAAAGAATGA
251 ATGAATGAAT GGATGAATGA ATGAATGAAT GAGAAGACAG AGAGAGAGAA
301 GGAAGGAAGG AAGGAAGGAA GGAAGGAAGG AAGGAAGGAA AGAAAGAAAA
351 GAAAAGAAAG AAGAGAGAAA GAGAGAAAGA AAGAAAGAGA GAAAGAGAGA
401 GAGAGAGAGA GAGAAAGAGA GAGAGGAAGA GAAGAAGTCC TCTTAAAAAA
451 TAGCCTGAGA AACTGGGCTA TGTTGGCTTT TTTTTTTTTC TGTCAGTAGG
501 AAATATTTAT TCAACCTCAC TGCTAAAAAA AAACCAAAAC AAACAAACAA
551 AAAAACCTAA TAATTTCAGG AAAGCTGCTG TTTCTCGTGT TCTGATC
       SEQUENCE: 20 corresponds to wg1f2; Length 350 (SEQ ID NO: 20)

5' GATCACGCCA CTGCACTCCA GCCTGGGTGA CAGTGTGAGA CCCTGTCAAG
 51 GAACGAACGA AGGAAGGAAG GAAGGAAGGA AGGAAGGAAG GAAGGAAGGA
101 AGGAAGGAAG GAAGGAAGGA AGGAGGGAAG GAAGGAAAGA AGGCAGGCAG
151 GCAGGCAGGC AGGAAGGAAG GAAGGAAAGA AGGAAGGAAG GAAAGAAGGA
201 AGGAAGGAAA GAAGGAAGGA AGGTAGGAAG GTAGGAAGGA AGGAAGGAAG
251 GAAAGAAGGA AGGAAGGAAG GCAGTCAGGG AGNAAGGAAG GAAGGCAGGC
301 AGGCAGGCAG GCAGGCAGGC AGGCTTGCAA ATGTAGTTAA GTTAAAGATC
       SEQUENCE: 21 corresponds to wg1f4; Length 283 (SEQ ID NO: 21)

5' GATCATGCGG GCAGCTTTGG GGTATTTCAG ACGGTGTGGG GAGCATGGTC
 51 TGAATGTGCC TTGCTCCGGC AGCAGCATGC AGTAGTGGCA GTGGTACTTA
101 GGGCATGTGA GAGCACCCTG CCTCTCCTAT CCCTGACCCA GCAGCATGCA
151 GTAGCGGCAG TGGTACTTAG GGCATGTGAG AGCACCCAGC CTCTCCTATC
201 CCTGACCCAG CAGCTGGCAG CAGCAGCAGC AGCAGCAGCA GCAGCAGCCG
251 CCTCAGGGCA GGAGGCAGAG CCTTCAGGCG TGG
       SEQUENCE: 22 corresponds to wg1g5; Length 494 (SEQ ID NO: 22)

5' GATCACTGCA CTCCAGCCTG GGTGACAGAA TAAGACGAAA GAGAGAAAGA
 51 GAGAGGGAAA GAAAGAAAGA GAGAGAGAGA GAGAGAGAGA GAGAGAGAAA
101 GAAAGAAAGA AAGAAAGAAA GAAAGAAGAA AGCAAGAAGG AAGGAAGGAA
151 GGAAAGAAAG CAGCAGAAAA AGAGGAAGGG AGGGAGGAAG GAAGGAAGGA
201 AGGAAGGGAG GGAGGGAAGG AAGGAAGGAA GGAAGGAAGG AAGGAAGGAA
251 GGAAGGAAGG AAAGAGAGAG AGAGAAAGAA AATANNNNNN NNNNNNAACT
301 CCNNNAAACC CACAATTCAG ACACACAGCT CACACACAGG TCTCCAGCAT
351 AGACATATTT ATACATCCAT TTACTCAAAC ACTCACAATA CAATCACATA
401 AAACAGGCAG ACAGTTCACA TGCCAACACA CTCTTGCACA GACACGCAAA
451 CAGAAGCATG GAATTTGTAC AGAGCACGCT CACAGTGTCT GATC
       SEQUENCE: 23 corresponds to wg1g9; Length 301 (SEQ ID NO: 23)

5' GATCGTGCCA CTGTACCCCA GCCTGGGCTA CAGAGCGAGA CTCCATCTCA
 51 AAAAAAAAAA AGAAAGAAAG AAAGAGAGAA AGAGAGAGAG AGAGATGAAA
101 GAAAGAGAGA GAGGGAAAGA AAGGAAGGAA GGAAGGAAGG AAGGAAGGAA
151 GGAAGGAAGG CAGGCAGGCA GGCAGGCAGG CAGGCAGGCA GGCAGGCAGG
201 CGGACAGCAA GAAGACACCG TTTTGCCATG AGGTTAGACA CGCGGACAGG
251 CACAGAGCAG ACGCACGTGC ACCATGCTAT CATGGCAGGA CAGGTTCACA
301 T
       SEQUENCE: 24 corresponds to wg1h10; Length 538 (SEQ ID NO: 24)

5' GATCATCAAA ATACAATTAT AGAAATATTT ATAAGCAGCA TTATTCATAA
 51 TCGCCAAAAA CTGGAAGCAG TGCGATGGCA AAATAGATGC ATAAATGGTG
101 ATAAGTATAA GAGGGGAAGA AAGAATGAAA GAAAGAATGG AAGGAAGGAA
151 GGAAGGAGGG AAGGAAGGAA GGAGGGAAGG AAGGAGGGAA GGAAGGAGGG
201 AAGGAGGGAA GGAAGGAGGG AAGGAAGGAA GGGAGGAAGG GAGGGAGGGA
251 GGGAGGGAGG AAGGGAGGGA GGGAGGGAGG GAGGGAGGGA AAGGACTAGA
301 GGGTGGAAGA TAGGGAGAGA AACAAGTAAA TAAGCTAGCT CTTTCCTAGA
351 AAATAATTTC ACCAACGTTT CTGTGACATT CAAGAAAACA ACTGGGACTT
401 GGAAACAATT AAAAATAAAT AAACAAAAGT ATGCCACTAG ACTCTAAAGT
451 CAGTGGTGTG GGAAGCAGAG GTTATCAGTG TTCAGAGGAG AGAAGACTCC
501 CACAGAATAG GGCTGTCAGG AATGAGCTCA GGGAGGAA
       SEQUENCE: 25 corresponds to wg2a5; Length 421 (SEQ ID NO: 25)

5' GATCACCTGA GGTCAGGAGT TTGAGACCAG CCTGGACAAC ATGACAAAAC
 51 CCCTATCTAA AAAAAAAGAA ATAGCTAGGC ATGGTGGTGT GCACCTGTAG
101 TCCCAGCTAC TTGGGAGGCT GAGGCAGAGA ATCACTTGAA CCCGGGAGGC
151 AGAGGTTGCA GTGAGCCGAG GAGGCGCCAC TTCACTCCAG CCTCTGTCTC
201 CAAAGAAAGA AAGGAAAAGA AAGAAGGAAA GAAAGAGAGA GGGAGGAAAG
251 AAGGGGAGGA AGGAAGGAAG GAAGGAAGGA AGGAAGGAAG GGAGGGAGGG
301 AGGGGAGGAG GGAGGGAGGG AGGGAGGGAG GGAGGGAAAA AGAAAAGAGG
351 TGAGCACACG GTTACATTGA GGAAAACAAA GATGAAACTT CACATCACAT
401 TCCAACAAGT CACAGCTTGA T
       SEQUENCE: 26 corresponds to wg2b3; Length 446 (SEQ ID NO: 26)

5' GATCTCAGGT GACCCACCAG CCTCAGCCTC CCAAAGTGCT GGGATTACAG
 51 GCCTGTGCCA CTGCACCCAG CCATCTGTTC AGTACTTTCA TTATAAGAGA
101 GAAAGGAGGA GAGGGAAGGG AAGGGAGGGA AGGGGAGGGG AAGGGAATCA
151 ATGGGAAAGG AGGGTCAAGA AGGAGAAGGA GAGAAGGAAG GAAGGGAGGG
201 AGGAAGAGAG GAAGGAAGGA AGGAAAGAAG GAGGGAAGGA AGGAAGGAAA
251 GAAGGAGGGA AGGAAGGAAG GAGGGAGGAG GGAAGGAAGG AAGGAAGGAA
```

```
301 AGAAGGAAGG AAGGAAGGAA AGAGGGAAGA AAGGAAGGAA GGAAAGAAAG
351 AAGGGAGGAA GGGAGGGAGG GAGGGAGGGA ATGAGTGGNA GAAGCCAAGT
401 CTGCAGTTGG GAAATCATGG GACGTGCTGG CTTTTCCTCT CTGATC
        SEQUENCE: 27 corresponds to wg2c9; Length 287 (SEQ ID NO: 27)
```

```
  5' GATCACTTGA GCCCAGGAGT TCAAGGCTGT GGTAAACTAT AATCACACTA
 51 CTGCACTCCA GCCTGGGTGA CAGAGAAAGA CCCTGTCTCA AAAAAGGAAG
101 GAAAGAAGGA AGGAAGGAAG GAAGGAAGGA GGGAGGGAGG GAGGGAGGAA
151 GGGAGGGAGG GAGGGAAGGA GGGAAGGAAG GAAGGAAGGA AGGAAGGAAG
201 GAAGGAAATA GCAGCTCTGA GCTTAGAAAA AGGAGTCTAT TTCTAAGTGG
251 GAGATGGGGA GAAGGAGGGA ACTGGGGAGG TGAGGAA
        SEQUENCE: 28 corresponds to wg0c5; Length 252 (SEQ ID NO: 28)
```

```
  5' GATCATTAGG TTGAAAAAGA GCTAAAAGAT GAAACCGATT GGCACTGGTG
 51 TGTGGTGGTG GTGGAGGAGG TGGTGGTGGC GGCGGCGGTG GTGGTGGTGG
101 TGGTGGTGGT GGTGGCGGTG GTGGTGGTAG GAATTACTCA AGTTACTGGA
151 AACATGCTGG TATCTTTTTT TAGTTTAGGT AGTAAACCTG GTAATGAACA
201 CTAAGTCAAA CAACAAATAC TAATTTCCAT CTCATGCACA AATGATATGA
251 AA
        SEQUENCE: 29 corresponds to wg0f4; Length 329 (SEQ ID NO: 29)
```

```
  5' GATCAGACAC TCTAAAGTCA CATTCCTTTA GAGGAACTGG ACAATCAAAT
 51 TTTGATGGTG TTCTAATGGT TTGTAAGGCA ACAAAACACA AAACTTTGTG
101 GTGGTGGTGG TGGTGGTGGT GGTGGTGGTG GTGGTATCTT CCATCACTTG
151 CCAAGGGCTT AGCCTGGACC TGCACACTCA CTATCTCCTT GACCATTTGC
201 ACCATCACCA GGAGGGAGGC ACTAGGTCCC CCGTTCTCAC TGTTATAAAT
251 AACAAACAGG TCTCCAAGGG GTGAGTAACT TTCTCGTGGA CACACAGAGG
301 CAGGTCTAGG ATTTGAACCC AGTTTGTCT
        SEQUENCE: 30 corresponds to wg0f5; Length 276 (SEQ ID NO: 30)
```

```
  5' GATCTCTCTA GGTCCTATTC TCTTTCAACC CTCTAGGGAA CTCAGGAAAC
 51 ATTGGGCTAT TGTCCATAAT GTGGTGATGG TGGTGGTGAT GGTGGTGGTG
101 GTGGCGGTGA TGGCAGCGGC AGTGGTGATG GCGATGGCGG CAGCGGCGGT
151 GGTGGTGGTG GTGTCACCCG AGGCTGCCTT GGTCCAGCCA GCACGCAGCC
201 TTCTCTATTC ATTCTCTCTT GTGTGGACCC GTGGGGGAAT TCTATGAGTC
251 TTGCCACTTC ANGGCTCCAC TCAGAA
    SEQUENCE: 31 corresponds to the first part of wg2e7; Length 185 (SEQ ID NO: 31)
```

```
  5' GATCATAGAG CAGGTCACCA GGATGAAGAC TGCATGAAGG CAAGGGCTTT
 51 GATGTACTCA TTGTCCTGGC CCCGGCATGG AGGTGCTGGA AGGCAAGAGG
101 GAGGAGGAGG GAGGCAGAGA TGGAAGGATG AAGGAGAAGA AGGAAGGAAG
151 GAAGGAAGGG AAGGAGGGAG GGACAGAGGG AGGAT
    SEQUENCE: 32 corresponds to the second part of wg2e7; Length 22 (bases 193–214)
                              (SEQ ID NO: 32)
```

```
  5' GGAAAGTTTT TTTAAAAAGA TC
    SEQUENCE: 33 corresponds to the first part of wg2f7; Length 140 (SEQ ID NO: 33)
```

```
  5' GATCTACATG CATAGTTTAT TTTTTATGTT CTTTTATGTT TGTTAATATG
 51 TAAATATATT TGTGATATAT TATTAAGTNA GAATATCAAC NGCCTTCCTT
101 CTTTCCNNCC CTCCCCACTT CCCTNCCTTN CCTTCCCAGC
        SEQUENCE: 34 corresponds to the second part of wg2f7; Length
                  211 (bases 144–354) (SEQ ID NO: 34)
```

```
  5' TCTGACAAGG TCTGTCTCTG TCACCTAGGC TAGAATGCAG TGGTGNAATC
 51 AATAGCTCAC TGCAGCCTTG ACCTTATGGA CTCAAGTAAT CCTCCTACCT
101 CAGNNTCCNN ACAGNNGGGA CCTCAGGTGC ATACCACGCT CTGCTAATTT
151 ATAGAGATGG AGTCTTACCA TTTTGCCTAA GATGGTCTCC AACTCCCGGG
201 TTCAAGTGAT C
        SEQUENCE: 35 corresponds to wg2f10; Length 374 (SEQ ID NO: 35)
```

```
  5' GATCTTGGCT GGGTCAACAC TCCTTCCTGG GCTTCAGTTT CTCATCTAAG
 51 AAGAGAGAGT TGGAGGATTG TGGTGGGGGG TTGGTCAGTG AAGGTAGGCA
101 TCCCAGGGTG GGTANCCATG AGGGTCTCTC TAGTCCTTTT TTCTTCTTCA
151 CCCTTACACT TATCCACCCA TCCAACCATC CATCCATCCA TCCATCCATC
201 CATCCATCCA TCCATTTTTT CTTTTTTCTT TTTTTCTTTT TTTGAGATGG
251 AGTCTTGCTC TGTTGCCCAG GCTGGAGTGC AGTGGCATGA TGTCAGCTCA
301 CTGCAACCTC TGCCTCCTGA GTTAGAGTGA TTTTCCTGCC TCAGCCTCCT
351 GAGTAGCTGG GACTATAGGC ACAC
            SEQUENCE: 36 corresponds to the first part of wg2g4;
                        Length 106 (SEQ ID NO: 36)
```

```
  5' GATCACCTGA GGGAGCTCAA GACCAGCCTG GCCAACATGA TGAAACCCCG
 51 TATATACTAA AAAGTACAAA AAATCANNNG GGTGTGTGGT GGGANTGTAA
101 TNTTAG
        SEQUENCE: 37 corresponds to the second part of wg2g4;
                  Length 124 (bases 114–237) (SEQ ID NO: 37)
```

```
  5' GAAAGAAAGA AAGAAAGAAA GAAAGCAAGC AAGCAAGCAA GCAAGCAAGC
 51 AAGCAAGCAG GCAGGCAAGN NAGCGGCGTC ACGCCNGTAA TCCCAGCACT
```

```
101 TTGGGAGGCC GAGGCGGGCA GATC
         SEQUENCE: 38 corresponds to the first part of wg2g12;
                    Length 213 (SEQ ID NO: 38)
```

```
  5' GATCATTTCC CAGTACATAA GGACCTGTTT CTCTCCTGCT AACATTAACC
 51 CTACTTGAGA CTTAGAGAAA GAGGCATCAC ACTTGAAAGT CTCCTGTGGG
101 TATAATGTCT ACTCTTTGTT TCATGAAAGG ATATCCTGGG GTGGTAGCTT
151 TTTGGTTTTC TTTCTCTCTT TCTCTCTTTC TTTCTTTCTT TCTTTCTTTT
201 CTTTCTTTCT TTC
         SEQUENCE: 39 corresponds to the second part of wg2g12;
                    Length 67 (bases 224–288) (SEQ ID NO: 39)
```

```
  5' TTCCTTCCNT CTTTTTTGTG GATGGAGTTC TGCTCTGTCA CCCTGGCTGG
 51 AGCGCAGTGG CACGATC
         SEQUENCE: 40 corresponds to the first part of wg2h11;
                    Length 97 (SEQ ID NO: 40)
```

```
  5' GATCGCACAC TGCACTCCAG CCTGGCAACA GAGGGAGACT TCATCAGAGA
 51 CAGAGAGAGA CAGAAAGAGA GAGAGATAGA GAAAGGGAGG GAGGGAG
         SEQUENCE: 41 corresponds to the second part of wg2h11;
                    Length 95 (bases 105–199) (SEQ ID NO: 41)
```

```
  5' AAGGAAGGAA AGAAGGAAGG AAGGAAGGAA GGAAAAAAGA AAAGAGAAAA
 51 AAAAAGGAGA GAGGTTGAAA AAAACAACTA CCTTGTGGTC AGATC
         SEQUENCE: 42 corresponds to wg3a6; Length 278 (SEQ ID NO: 42)
```

```
  5' GATCACTTAG CCTGGGAGGT TGAGGCTGCA GTGAGTCATG ATTTTGCCAC
 51 TACTGCATTC CAGCCTGAGT GACAGAGCCA ACCTGTCTTG AAAGAAAGAA
101 AGAAAAGAAA GAAGGAAAGA AAGAAAGAAA GAAAGAAAGA GAGAAAGAAA
151 GAAAGAAGGA AAGAAAGGAA GGGAAAGAAA GAAAGGAGGG AGGGAAGGAG
201 GGAGGGAGGG AAGGAGGGAG GGAGGGAGGG AGTATAAGAT GTATCCCCTT
251 AGCAAATGTT TAAATACACA GTATAGTT
         SEQUENCE: 43 corresponds to the first part of wg3b10;
                    Length 204 (SEQ ID NO: 43)
```

```
  5' GATCAAAACT GAGAAGCGCA AAGACAAAGA GTGTGCTTGT TGAATACCAA
 51 GTTGTATAGG CTGCAGAAGA GGAAGTGGTG GGACTGGAGT CTAGAGAGTC
101 TTGAACACCA GGTTTGGGAG TCTGGAGTTC ACTTGGTGAG TAACAATCTC
151 TGGCAGAGGA AGACTCCGTC TCAAAGAAAG AAAGAAAGAG AGAGAGAGAG
201 AGAG
         SEQUENCE: 44 corresponds to the second part of wg3b10;
                    Length 85 (bases 212–296) (SEQ ID NO: 44)
```

```
  5' AAAGAAAGAA AGAAAGAAAG AAAGAAAGAA AGAAAGAGAG GAAAGAAAGA
 51 AAGAAAAGAA AAAAAGGAAA GGAATGAAAG GGATC
         SEQUENCE: 45 corresponds to the first part of wg3f12;
                    Length 140 (SEQ ID NO: 45)
```

```
  5' GATCATGCTA CTGCACTCCT GCCTGGACGA CAGATTGAGA CCCCATCTCG
 51 GAAGGAAGGA AGGAAGGAAG GGAGGGAGGA AGGAAGGAAG GAAGGGAGGG
101 AGGGAGGGAG GAAGGGAGGG AGGGAGGGAG GGAGGAAAAC
         SEQUENCE: 46 corresponds to the second part of wg3f12;
                    Length 153 (bases 150–302) (SEQ ID NO: 46)
```

```
  5' ATAGAAAGTA AGAAAGAAAG GAAACAATTG TGTGATGCAC AGCTTTGTGC
 51 AGTGAGGNTT TTTTTGCCTC CAAGGTTTTG GGACAAGAAG GCACACAGAG
101 AATTAAAGGA GTCCAGAGTT ACTTGCTGTC CTGATATAGA TCCACTAGTT
150 CTA
         SEQUENCE: 47 corresponds to wg3h2; Length 278 (SEQ ID NO: 47)
```

```
  5' GATCTTTTTG GCTTTTTGGC ATAACATGGC TGGCAGAGCT CAAATTGTTT
 51 TTATCAGCTT AGTTACCTCT ACCCAGTAGA AATACAACTG CTGAAATTGT
101 AATTAGGTCT TTTATATTCC TCTCCTTCCT CCCTCCCTCC CTCCCTCCCT
151 CCGTCCCTCC CTTCCTCCCT TCCTTCCTTC CTTTCTTCCC TACCCCCCTC
201 TCTTTCTTCT TTTTATTTCC TTGTTTATTT CTGTCTAGCA CTAGATTTCA
251 TGGGAGACAT AGACTAAGAT ATAAATTT
```

TABLE 1

|                        | Triplet | Tetramer | Total |
|------------------------|---------|----------|-------|
| Repeats not seen       | —       | —        | 5     |
| Loci represented twice | 2       | 1        | 3     |
| District repeat arrays | 19      | 27       | 46    |
| Number polymorphic     | 6       | 18       | 24    |

TABLE 2

| Clone | Major Repeat(s) | No. of Alleles | Heterozygosity (%) | Size Range | Chromosome | Interval | EMBL | GDB |
|---|---|---|---|---|---|---|---|---|
| wg0e7 | AYC | 4 | 50 | 265–330 | 12 | — | X73968 | D12S387 |
| wg1a2 | AARG | 7 | 80 | 435–480 | 7 | D7S369–D7S129 | X74431/2 | D7S808 |
| wg1a3 | AAAG | 10 | 85 | 414–462 | 20 | OXT-D20S27 | X75550/1 | D20S212 |
| wg1a9 | RRC | 2 | 30 | 101–104 | X | DXS178–DXS100 | X73287 | DXS1252 |
| wg1c3 | GGC | 2 | 30 | 97–106 | 10 | D10S7–D10S58 | X76102 | (eIF4D?) |
| wg1c5 | AWGG | 7 | 90 | 294–318 | 14 | D14S53–D14S18 | X73288 | D14S299 |
| wg1d1 | AGGR | 8 | 90 | 186–218 | 15 | CYP1A1-D15S37 | X75552 | D15S233 |
| wg1d5 | AGGR | 7 | 70 | 210–234 | 22 | D22S257-PDGFB | X74779 | D22S442 |
| wg1d6 | AGC | 2 | 40 | 72–75 | 4 | D4S174–D4S1 | X73289 | D4S1639 |
| wg1d10 | AGC | 2 | 25 | 85–97 | 2 | D2S44–D2S103 | X74433 | D2S419 |
| wg1d11 | AAGG | 2 | 20 | 402–417 | 15 | ACTC-D15S35 | X75553/4 | |
| wg1e4 | AGGR | 2 | 60 | 263–267 | 1 | D1S81–D1S51 | X74434 | D1S525 |
| wg1e7 | AAGG | 4 | 70 | 110–122 | 3 | D3S13–D3S20 | X74780 | D3S1749 |
| wg1e12 | AAKG | 9 | 75 | 266–298 | 7 | D7S96–D7S129 | X75555 | D7S822 |
| wg1f2 | AAGG | 13 | 90 | 280–502 | 16 | HP-D16S43 | X75556 | D16S543 |
| wg1f4 | AGC | 2 | 30 | 71–74 | 6 | — | X73969 | D6S483 |
| wg1g5 | AGRR | 11 | 85 | 301–374 | 19 | — | X74435 | D19S428 |
| wg1g9 | AGGS | 9 | 95 | 241–289 | 7 | D7S81–D7S129 | X73290 | D7S809 |
| wg1h10 | RRGG | 6 | 50 | 247–311 | 18 | — | X74781 | D18S555 |
| wg2b3 | ARGG | 2 | 50 | 360–380 | 20 | D20S18–D20S17 | X74436 | D20S204 |
| wg2c9 | ARGG | 7 | 95 | 187–247 | 1 | D1S48–D1S68 | X73291 | D1S526 |
| wg0c5 | NCC | 3 | 9 | 118–144 | 3 | D3S13–D3S20 | X73967 | D3S1747 |
| wg0f4 | ACC | 3 | 28 | 84–93 | 18 | — | X73214 | D18S496 |
| wg0f5 | RYC | 2 | 53 | 208–217 | 2 | D2S48–D2S34 | X73125 | D2S413 |
| wg2e7 | | 4 | 53 | 340–372 | 20 | | | |
| wg2f7 | | 3 | 45 | 254–262 | 17 | | | |
| wg2f10 | | 2 | 50 | 230–234 | 19 | | | |
| wg2g12 | | | | | 2 | | | |
| wg2h11 | | 9 | 90 | 300–436 | 2 | | | |
| wg3a6 | | 12 | 90 | 227–275 | 11 | | | |
| wg3b10 | | 15 | 88 | 460–544 | 19 | | | |
| wg3f12 | | 5 | 71 | 240–280 | 11 | | | |
| wg3h2 | | 2 | 10 | 190–194 | 11 | | | |

TABLE 3

| Clone (locus) | Primer Names | Primer Pair | Primer Sequences (5' 3') | | | EMBL | T°C. |
|---|---|---|---|---|---|---|---|
| wg0e7 (D12S387) | wg0e7a wg0e7b | 1 | GCACACTGGA AGCCATGGTA | AGTGCAAGTA AGTCTTAATA | AC TATG | X73968 | 65 |
| wg1a2 (D7S808) | wg1a2a* wg1a2b | 2 | TCTTCTCATC AGTGAGACTC | TCTCAAGCAG CATCAAA | | X74431/2 | 58 |
| wg1a3 (D20S21252) | wg1a3a* wg1a3b | 3 | GATCCATCCA GATCCTGCCA | CCTTCCTC CTGCAATC | | X75550/1 | 67 |
| wg1c9 (DXS1252) | 2613 2614 | 4 | CTTTTAGTGG CCTGAGTTAT | GGTTACCTGG CCCAGGAGCC | C | X73287 | 67 |
| wg1c3 | 2740* 2789 | 5 | CTAAAAATCT AGCCCAACCG | CACTTGATAC CTGCCTC | TTG | X76102 | 60 |
| wg1c4 (D8S580) | 2735 2790* | 6 | GAGTGAGACT AGCTCTATCA | CCATCTCAAC GATTGGTTTG | G* | X74778 | 60 |
| wg1c1 (D15S233) | 2739 2811* | 8 | CACCACGTCC AGGTCTGGGT TCCA | CCCCTCTAAT GACAGAACA CTGTCTTGT | | X75552 | 62 |
| wg1d5 | 2737 | 9 | GACAGAGCGA | GACTCTGTCT | A | X74779 | 68 |

TABLE 3-continued

| Clone (locus) | Primer Names | Primer Pair | Primer Sequences (5' 3') | | | EMBL | T°C. |
|---|---|---|---|---|---|---|---|
| (D22S442) | 2791* | | CCTAGCTCCC | AGAACTTTCT | CC | | |
| wg1d6 (D4S1639) | 2649 2650 | 10 | AGGAACTGTG TGCCGATTAC | GTACAATAT CCTACTTCAT | TG C | X73289 | 67 |
| wg1d10 (D2S419) | wg1d10A wg1d10B | 11 | TAGCCTGCTT GGAGGGGGTC | ACCTTGAG ACTTTCTG | | X74433 | 55 |
| wg1d11 | 2746 2806 | 12 | TTGGGCCTAG TGACAAAGCC | AAGGGAACTG AGACCTTG | | X75553/4 | 62 |
| wg1e1 | 2745 2794* | 13 | ATAAGAGAGT ACAGCAAGAC | AAATTTCTGG TCCACCAA | TG | X75409 | 61 |
| wg1e4 (D1S525) | wg1e4A* wg1e4B | 14 | TGACTGCAGC ATCATGGCAG | GGGATTAATC TACAGTCC | | X74434 | 56 |
| wg1e7 (D3S1749) | 2744 2792 | 15 | GTGACAGTGC CCCTCCGTCT | AAGTTTCTGC CTCCCTGC | | X74780 | |
| wg1e12 (D7S822) | 2743 2808 | 16 | CTCCCTCCAC CATAGCCAG | TCTGGAAATC TTTCTCAGGC | | X75555 | |
| wg1f2 (D16S543) | wg1f2c* wg1f2e | 17 | GATCTTTAAC ACAGTGTGAG | TTAACTACAT ACCCTGTCAA | TTGCAAG GG | X75556 | 62 |
| wg1f4 (D6S483) | 2702 2703 | 18 | TATCCCTGAC CTGCCTCCTG | CCAGCAGCTG CCCTGAGGC | | X73969 | 67 |
| wg1g5 (D19S428) | wg1g5A wg1g5B* | 19 | GGGTGACAGA ATGTCTATGC | ATAAGACG TGGAGACCTG | | X74435 | 58 |
| wg1g9 (D7S809) | wg1g9A wg1g9B* | 20 | GATCGTGCCA CGCGTGTCTA | CTGTACC ACCTCATGGC | | X73290 | 62 |
| wg1h10 (D18S555) | 2741* 2795 | 21 | GTGCGATGGC ATTTTCTAGG | AAAATAGATG AAAGAGCTAG | C | X74781 | 60 |
| wg2a5 (D4S1640) | wg2a5A wg2a5B* | 22 | CTCCAGCCTC CTTGTTGGAA | TGTCTCC TGTGATGTGA | AG | X73970 | 62 |
| wg2b3 (D20S204) | wg2b3A wg2b3B* | 23 | CAGCCATCTG TGATTTCCCA | TTCAGTACTT ACTGCAGACT | TC TG | X74436 | 64 |
| wg2c9 (D1S526) | wg2c9A* wg2c9B | 24 | TCAAGGCTGT ATAGACTCCT | GGTAAACTAT TTTTCTAAGC | AATC TCAG | X73291 | 64 |
| wg0c5 (D3S1747) | 2099 2100 | 27 | AAAAAGAGCT TGTTTCCAGT | AAAAGATGAA AACTTGAGTA | ACCG ATTC | X73967 | 64 |
| wg0f4 (D1S5496) | 2101 2102 | 26 | ATGGTTTGTA GCCCTTGGCA | AGGCAACAAA AGTGATGGAA | ACAC G | X73214 | 64 |
| wg0F5 (D2s413) | 210321C4 | 27 | TCAGGAAACA AGTGGCAAGA | TTGGGCTATT CTCATAGAAT | GTCC TCCC | X73215 | 64 |
| wg2e7 | 3297 3298 | 28 | GCTTTGATGT GATCTTTTA | ACTCATTGTC AAAAAACTTT | CC | | 60 |
| wg2f7 | 3327 3328 | 29 | ATGTTCTTTT TGACAGAGAC | ATGTTTGTTA AGACCTTG | ATATG | | 63 |
| wg2f10 | WG2F10A WG2F10B | 30 | CCATGAGGGT CAGTGAGCTG | CTCTCTAGTC ACATCATG | | | 60 |
| wg2g4 | WG2G4A WG2G4B | 31 | ACCTGAGGGA GATCTGCCCG | GCTCAAGAC CCTCGG | | | 66 |
| wg2g12 | WG2G12A WG2G12B | 32 | TCATGAAAGG GAGCAGAACT | ATATCCTGGG CCATCCAC | | | 62 |
| wg2h11 | WG2H11A WG2H11B | 33 | AGAGGGAGAC GATCTGACCA | TTCATCAG CAAGGTAGTT | G | | 62 |
| wg3a6 | WG3A6A WG3A6B | 34 | GTCATGATTT ACATTTGCTA | TGCCACTACT AGGGGATACA | G TC | | 64 |
| wg3b10 | 3299 3300 | 35 | TGAGTAACAA GATCCCTTTC | TCTCTGGCAG ATTCCTTTCC | | | 60 |
| wgf12 | WG3F12A WG3F12B | 36 | GACAGATTGA GCACAAAGCT | GACCCCATC GTGCATCAC | | | 60 |
| wg3h2 | WG3H2A WG3H2B | 37 | TACCCAGTAG CATGAAATCT | AAATACAACT AGTGCTAGAC | GC AG | | 62 |

TABLE 4

| Clone | Sequence Number(s) |
|---|---|
| wg0e7 | 1 |
| wg1a2 | 2 & 3 |
| wg1a3 | 4 & 5 |
| wg1a9 | 6 |
| wg1c3 | 7 |
| wg1c4 | 8 |
| wg1c5 | 9 |
| wg1d1 | 10 |
| wg1d5 | 11 |
| wg1d6 | 12 |
| wg1d10 | 13 |
| wg1d11 | 14 & 15 |
| wg1e1 | 16 |
| wg1e4 | 17 |
| wg1e7 | 18 |
| wg1e12 | 19 |
| wg1f2 | 20 |
| wg1f4 | 21 |
| wg1g5 | 22 |
| wg1g9 | 23 |

TABLE 4-continued

| Clone | Sequence Number(s) |
|---|---|
| wg1h10 | 24 |
| wg2a5 | 25 |
| wg2b3 | 26 |
| wg2c9 | 27 |
| wg0c5 | 28 |
| wg0f4 | 29 |
| wg0f5 | 30 |
| wg2e7 | 31 & 32 |
| wg2f7 | 33 & 34 |
| wg2f10 | 35 |
| wg2g4 | 36 & 37 |
| wg2g12 | 38 & 39 |
| wg2h11 | 40 & 41 |
| wg3a6 | 42 |
| wg3b10 | 43 & 44 |

TABLE 4-continued

| Clone | Sequence Number(s) |
|---|---|
| wg3f12 | 45 & 46 |
| wg3h2 | 47 |

We claim:

1. A simple tandem repeat for use in a method of diagnosis of the human or animal body characterised in that it may be amplified at least in part by PCR using any one of primer pairs 3 (SEQ ID NO:56 and 57), 5 (SEQ ID NO:60 and 61), 8 (SEQ ID NO:66 and 67), 13 (SEQ ID NO:76 and 77), 16 (SEQ ID NO:82 and 83), 17 (SEQ ID NO:84 and 85), 21 (SEQ ID NO:92 and 93), 28 (SEQ ID NO:106 and 107), 29 (SEQ ID NO:108 and 109), 30 (SEQ ID NO:110 and 111), 31 (SEQ ID NO:112 and 113), 32 (SEQ ID NO:114 and 115), 33 (SEQ ID NO:116 and 117), 34 (SEO ID NQ:118 and 119), 35 (SEQ ID NO:120 and 121), 36 (SEQ ID NO:122 and 123), and 37 (SEQ ID NO:124 and 125).

2. A simple tandem repeat according to claim 1 consisting of at least one of sequences wg1a3 (SEQ ID NO:4 and 5), wg1c3 (SEQ ID NO:7), wg1d1 (SEQ ID NO:10), wg1e1 (SEO IQ NO:16), wg1e12 (SEQ ID NO:19), wq1f2 (SEQ ID NO:20), wg1h10 (SEQ ID NO:24), wg2e7 (SEQ ID NO:31 and 32), wg2f7 (SEQ ID NO:33 and 34), wg2f10 (SEQ ID NO:35), wg2g4 (SEQ ID NO:36 and 37), wg2g12 (SEO ID NO:38 and 39), wg2h11 (SEQ ID NO:40 and 41), wg3a6 (SEQ ID NO:42), wg3b10 (SEQ ID NO:43 and 44), wg3f12 (SEQ ID NO:45 and 46), and wg3h2 (SEQ ID NO:47).

3. A simple tandem repeat according to claim 2 wherein it is polymorphic.

4. A simple tandem repeat according to claim 3 wherein it has a heterozygosity of at least 80%.

5. A simple tandem repeat according to claim 4 wherein it has a heterozygosity of at least 85%.

6. A simple tandem repeat according to claim 5 wherein it has a heterozygosity of at least 90%.

7. A pair of amplification primers for use in a method of diagnosis of the human or animal body specific to any one of the simple tandem repeats in claim 1.

8. A pair of amplification primers according to claim 7 wherein they are PCR primers.

9. A nucleic acid probe for use in a method of diagnosis of the human or animal body comprising any one of the simple tandem repeats of claim 1.

10. A method of genetic characterization of the human or animal body wherein sample DNA is compared to reference DNA by using at least one of the simple tandem repeats or primers of claim 1.

11. A method of genetic characterization wherein sample DNA is compared to reference DNA using at least one pair of amplification primers of claim 7.

12. A method of genetic characterization according to claim 10 wherein it is a genetic mapping study.

13. A method of genetic characterization wherein sample DNA is compared to reference DNA using at least one probe of claim 9.

14. A pair of amplification primers for amplification of any one of the simple tandem repeats of claim 1.

15. A pair of amplification primers for use in a method of diagnosis of human or animal body, wherein said primers amplify any one of the simple tandem repeats of claim 1 in a polymerase chain reaction using an annealing temperature T° C., wherein T° C. is as shown in Table 3.

16. A nucleic probe for use in a method of diagnosis of the human or animal body comprising any one of the simple tandem repeats of claim 2.

17. A method of genetic characterization wherein sample DNA is compared to reference DNA using at least one pair of amplification primers of claim 15.

18. A method of genetic characterization wherein sample DNA is compared to reference DNA using at least one probe of claim 16.

* * * * *

SEQUENCE LISTING ( 1 ) GENERAL INFORMATION:

( i i i ) NUMBER OF SEQUENCES: 125

( 2 ) INFORMATION FOR SEQ ID NO:1:

( i ) SEQUENCE CHARACTERISTICS:
        ( A ) LENGTH: 377 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GATCAAATTT ATTCTCTCCT TTGCACACTG GAAGTGCAAG TAACATTTCT TCCTTCTCCT        60

GCTCCTCCTC CTGATAACAA TGGTGATGAT GATGGTGATG ATGGTGGTGG TGATGGTGAT       120

GTTGGTGGTG ATGATGGTGA TGGTGATGGT GGTGATGATG GTGGTGGTGA TGGTGGTGGT       180

GATGGTGGTG GTGATGGGGT GGTGACGGTG ATGTTGACGG TGGTGGTGGT GGTGGTGATG       240

GAGTGGTGAT GGAGTGGTGA TGATGGTGGT GATGGTGGTG ATGGCGATAA CAAACATATA       300

TTAAGACCTT ACCATGGCTR GGCATGGTGG CTGATRCCTG TAATCCCAGC ACTTTGGGAG       360

GCCGAGGCGG GCAGATC                                                     377
```

( 2 ) INFORMATION FOR SEQ ID NO:2:

( i ) SEQUENCE CHARACTERISTICS:
        ( A ) LENGTH: 346 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GATCATTCGG AAGAAAGTGT GGAAGCAGCA GCAAAGAGTG GAAAATGAAA AGAGAAACTC        60

TGGAGAAGGC AAGGTGGGCA GGAGCAGGAC TGTGCCGCCT GCACCCATGC AGGCTAGGCG       120

TTGTCCAACA CTGGGGCACC CGTCACTCAG ATTGAGATGA GGACAATGA GAGGAGCCTG       180

GAGGAGAGCT CCACACAAAT AAAGGGAGAA GCCTATGCAG GGCTGGAGA TTCCTTCTGT       240

GGTGACAGAG CATGGCATAG TTAGATTCAC AGACTNNNNN NAGATCGAGA GAATGATGCG       300
```

TGCTCTTCTC ATCTCTCAAG CAGCAATGCA GGGGGAACAT CAGCTG                    346

( 2 ) INFORMATION FOR SEQ ID NO:3:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TTGTTTTTTT GATGGAGTCT CACTCTGTTG CCCAGGCTGG AGTGCAGTGG CGTGATC        57

( 2 ) INFORMATION FOR SEQ ID NO:4:

( i ) SEQUENCE CHARACTERISTICS:
        ( A ) LENGTH: 217 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GATCCATCCA TCCTTCCTCC CTCCTTCCCT CTCTTTCTAC CTCTTTCTCG CTCTCTCTTT    60

CTTCCTTCCT TCCTCCCTCC CTCCCTCCTT CCCTCCCTCC CTTCCTCCCG CCCTCCTTCC    120

CTTTTCCCTT CCCCCTTCCT CTTTCTTTCT CTTTCTTTCT CTTTCTTTCT TACTTTCTTT    180

CTTTCTTTCT TTCTTTCTTT CTTTCTTTCT TTCTTTC                             217

( 2 ) INFORMATION FOR SEQ ID NO:5:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GAGTCTCACT CTGTTGCCCA GGCTGGATTG CAGTGGCAGG ATC                      43

( 2 ) INFORMATION FOR SEQ ID NO:6:

( i ) SEQUENCE CHARACTERISTICS:
        ( A ) LENGTH: 286 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GATCAGTTTC TGACTGCTGG GCGGGACAAA GCCTCCTGAA GTTGCTGCGA GGCACCTCCC    60

CCTGTGAGCA GAGCTTGGTA CAGCCCAAAT AGTTTTCAGG TTAAGAAAGC CAGAATCTTT    120

GTTCAGCCAC ACTGACTGAA CAGACTTTTA GTGGGGTTAC CTGGCTAACA GCAGCAGCGG    180

CAACGGCAGC AGCAGCAGCA GCAGCAGCAG CAGCAGCAGC AGGGCTCCTG GGATAACTCA    240

GGTGAGTAGA GAGGGAATTC GCAAACTTAC CCTGGAGTTT TATTTC                   286

( 2 ) INFORMATION FOR SEQ ID NO:7:

( i ) SEQUENCE CHARACTERISTICS:

(A) LENGTH: 457 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

| | | | | | | |
|---|---|---|---|---|---|---|
| GATCCAATGG | CTCTTTAGTC | AGGGTGTTAT | GTCCTGAAAA | TAGGTGACAA | CTGCAAACCA | 60 |
| TCCTCTGGTG | TCCAGAGACT | TAACAAGGT | TTGTTTCACA | GAGACTGAGG | GCAGAAAAAA | 120 |
| GGAAATGGCC | TAAAAAGGTG | GGTTTGCTGT | GTTGCCTCAC | ACTACTTGAT | TCATGGTTCT | 180 |
| GATTCTAAAA | ATCTCACTTG | ATACTTGATT | TCATATGAAA | GACGTGTAAA | ATGCCTGGGT | 240 |
| AGAGGCGGCG | GCGGCGGCGG | CGGCGGGCTC | GGAGGCAGCG | GTTGGGCTCG | CGGCGAGCGG | 300 |
| ACGGGGTCGA | GTCAGTGCCG | TTTGCGCCGG | TTGGAATCGA | AGCCTCTTAA | AATGGCAGAT | 360 |
| GATTTGGACT | TCGAGACAGG | AGATGCAGGG | GCCTCAGCCA | CCTTCCAAT | GCAGTGCTCA | 420 |
| GCATTACGTA | AGAATGGCTT | TGTGGTGCTT | AAAGGCT | | | 457 |

(2) INFORMATION FOR SEQ ID NO:8:

(i) SEQUENCE CHARACTERISTICS:
(A) LENGTH: 370 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

| | | | | | | |
|---|---|---|---|---|---|---|
| GATCACACCA | TTGCACTCCA | GCTTGGGCAA | CAGAGTGAGA | CTCCATCTCA | ACAAAAAAA | 60 |
| GAAAGAAAAG | AAAAGAAAGA | AAGAAAAGA | AAGAAAAGA | AAGAGAAAGA | AAGAGAAAA | 120 |
| GAAAGAAGGA | AGGAAGGAAG | GAAGGAAGGA | AGGAAGGAAG | GAAGGGAGGA | AGGAAGGAAG | 180 |
| GAAAGCAAGA | AAGAAAGAAA | GAAAGAAAGA | AAGAGAAAGA | AAGAAACTAT | CCAAACCAAT | 240 |
| CTGATAGAGC | TGAAAAACTT | ACTACAAGAA | TTTCATAATA | CAATCAGAAG | TATTAACAAC | 300 |
| AAAATGCACC | AAGCTAAGGA | AAGAATCTCA | GAACTAGAAG | ACCCAGTTCT | TTGAATCTAT | 360 |
| TCAGACAGAC | | | | | | 370 |

(2) INFORMATION FOR SEQ ID NO:9:

(i) SEQUENCE CHARACTERISTICS:
(A) LENGTH: 367 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

| | | | | | | |
|---|---|---|---|---|---|---|
| GATCTCAATA | AACATTGATA | CTGGAGGGAT | GAAATGAAGG | AAGGATGGAT | AGAAGGCTAT | 60 |
| AAGGATGGGT | GGATGGATAA | ATGGATGGAT | GGATGGATGG | ATGGATGGAT | GGATGGATAG | 120 |
| ATGGATGGAT | GGAAAAATGG | ATAGATGGAT | GGGTGGATGG | ATGAATGGAT | GGATGGATGG | 180 |
| ATGGATGGAT | GGATGGGTGG | ATGGATGAAT | ATATTGGGTG | GATGGATGGA | AGGAAGGAAG | 240 |
| GAAGGAAGGA | AGGAAGGAAG | GAAGGAAGGA | AGGATGGTAG | AAGAAAGGTA | GTACCAGTAT | 300 |
| GCTTTAGCTC | ATGCAGGCAA | ACAGATGATG | GGCAGAGGGA | AGCATGGTGG | CTGATTACAG | 360 |
| GAGGATC | | | | | | 367 |

( 2 ) INFORMATION FOR SEQ ID NO:10:

( i ) SEQUENCE CHARACTERISTICS:
        ( A ) LENGTH: 434 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
GATCCTCTTG  CCTAGGCCTC  CCAAAGTGCT  GGGATTACAG  GCAAGAGCCA  CCACGTCCCG   60
CCTCTAATTT  CTCTCCTCTT  CTCTCCTCTC  CTTTCCTTTC  CTCTCCTCTC  CTTTCCTTTC  120
CTCTTCTCTT  CTTGTTTTTT  TCTTTTCTNC  CCTCCCTCCC  TCCCTCCCTC  CCTCCCTCCC  180
TCCTTCCTTC  CTTCCTTCCT  TCCTTCCTTC  CTTCCTTCCT  TCCTTCCTTT  TGAGACAGA   240
GTTTTGTTCT  GTCACCCAGA  CCTGAGTGCA  ATGGGCACAA  TTTTGGCTCA  CTGCAACCTC  300
CATCTCCCCG  GTTCAAGTGA  TTCTTCTGCC  TTAGCCTCCC  GAATAGCTGG  AACTACAGGC  360
ACCTGCCACC  ATGCCCCAGC  TAATTTTTTG  TATTCTCAGT  AGAGATGGGG  TTTACCATGT  420
TGGCCAGGCT  GCTC                                                        434
```

( 2 ) INFORMATION FOR SEQ ID NO:11:

( i ) SEQUENCE CHARACTERISTICS:
        ( A ) LENGTH: 325 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
GATCGCGCCA  CTGTACTCCA  GCCTGGGCGA  CAGAGCGAGA  CTCTGTCTAA  AAAAAAGAA    60
AAAGAAAAA   AAAGAAAGAA  TGAGAGAAAG  AGAGAAGGAA  GGAAGGAAGG  AAAAGGAAAG  120
AGAGAGAGGA  AGGAAGGAAG  GAAGGAAGGA  AGGAAGGAAG  GAAGGAAGGA  AGGAAGGGAG  180
GGAGGGAGGG  AGGGAGGGAG  GGAGGGAGGG  AGGGAAAGGC  AGGGAGAAAG  TTCTGGGAGC  240
TAGGGAGTGC  CCGGGGTGGG  GAGCTCCAAG  AACAAGCCCC  AGGGAGCTGT  AACAAAGACT  300
TTGTCACAGC  TAGCCTGAAG  CTAGC                                           325
```

( 2 ) INFORMATION FOR SEQ ID NO:12:

( i ) SEQUENCE CHARACTERISTICS:
        ( A ) LENGTH: 263 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
GATCCCACCT  GCCATACGGT  GGGATTTCTA  GGACTATACA  AATGACAGAA  GGGTAGTAAG   60
AGGAAGACTG  TGTTGCTTAA  TGAGGTTTCC  AGAAATTGGT  AATGATATTT  GTAATTCCAA  120
ATCCTACTAC  AAGGAACTGT  GGCTACAATA  TTGATGCTGC  TGCTGCTGCT  GCTGCTAATT  180
TGATGAAGTA  GGCTAATCCG  CATGGCTACA  TCTCTGTATT  AGTCCATTCT  CGCGCTGCTA  240
TAAAGAAACT  ACCTGTGACT  GGG                                             263
```

( 2 ) INFORMATION FOR SEQ ID NO:13:

( i ) SEQUENCE CHARACTERISTICS:

(A) LENGTH: 160 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

| | | | | | | |
|---|---|---|---|---|---|---|
| GATCCTGTTC | ATGGTACAAA | GCTTTCCCTA | GCAGCCTGCC | CTCCCTAGCC | TGCTTACCTT | 60 |
| GAGNNGAGAG | GAAGCTGAAG | TAGCAGCAGC | AGCAGCAGCA | GCAGCAGAGT | TNCCAGAAAG | 120 |
| TGACCCCCTC | CCCTGAACAC | AGCAGGAAGC | AGCAGTCCAA | | | 160 |

(2) INFORMATION FOR SEQ ID NO:14:

(i) SEQUENCE CHARACTERISTICS:
(A) LENGTH: 238 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

| | | | | | | |
|---|---|---|---|---|---|---|
| GATCATTTCA | GTCTGCACAA | GAATGCTTGG | CCTTTTAATT | CCAACTTCAC | AGTTGAGAAA | 60 |
| ACTGATACTC | AAGGCAAAGA | ATCTTCTCAG | TAGTCAGAGT | CAATAACTGC | AGGAACTAAG | 120 |
| ACTGGAACCC | AAGTTTTCTG | CCTGGTATGT | TGGGCCTAGA | AGGGAACTGC | TATTCCTATC | 180 |
| TCTCCATCTT | TCCTTCCATC | TTTCCTTCCT | TCCTTCCTTC | CTTAATCCTT | CCTTCCTT | 238 |

(2) INFORMATION FOR SEQ ID NO:15:

(i) SEQUENCE CHARACTERISTICS:
(A) LENGTH: 120 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

| | | | | | | |
|---|---|---|---|---|---|---|
| TTCCTCTCTC | ACTGTCTCCC | TCNCTCTCTG | TCTCCCTCCT | TCCTTTCTTC | ACCTTCTTTC | 60 |
| TACTTTTTTA | AGAAACAAGG | TCTGGCTTTG | TCACCCAGGC | TGGAGTGCAG | TGGCGTGATC | 120 |

(2) INFORMATION FOR SEQ ID NO:16:

(i) SEQUENCE CHARACTERISTICS:
(A) LENGTH: 445 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

| | | | | | | |
|---|---|---|---|---|---|---|
| GATCTTGAGA | CAGGGTCATC | CTGGATTACT | GGAGTGTGCC | CTAAATCCAT | TGACAAGTGT | 60 |
| CCTTAGGAGA | GACGCAGAGT | GGAGGCACAC | AGTGGGAGGA | CGAGGCCACT | TGAAGACTGA | 120 |
| GGCCGGGATT | GCAGCGATGC | AGCCACAACC | CAGGAAAGTC | CGGGGCCACC | AGCGGCTGGA | 180 |
| AAAGGCAAGG | GAGGGGTCTT | CTGGCTCTTC | AACAATAAGA | GAGTAAATTT | CTGGTGTTTT | 240 |
| AAGCCACCTG | GTTTGTGGTG | CTTTTTCCTT | CCCTCCTTCC | TTCCTTCCTT | CCTTCCTTCC | 300 |
| TTCCTTCCTT | CCTTCCTTCC | TTCCTTCCCT | CCCTCCCTCC | CTCCCTCTCT | CCCTCCCTCC | 360 |
| CTCCCTTCCT | TCCTCTTCTT | TTTCTCTCCC | TCTCTCCTTT | TTTTCTTTTT | TTTGGTGGAG | 420 |

```
TCTTGCTGTG  TCGCCCAGGC  TGGAG                                                              445
```

(2) INFORMATION FOR SEQ ID NO:17:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
GATCCCAAAA  TACTGGCCTC  TCATAGTGAT  AGATTTAAAA  GATTGCTTCT  TTACCATTCC    60
TTTAGCTACC  CAAGATTATG  AAAAATTTGC  TTTTACTGTT  CCTTCTATAA  ATAACAAGA    120
ACCAGTGGAC  AGATACCATT  GGAAAGTACT  GCCACAAGGC  ATGCTAAATA  GCCCGACTAT   180
TTGTCAAACT  TATATCGGAA  AAGTTATGAA  GCCAATTAAA  GAACAATTTT  ACAAATGTTA   240
TATTATCCAT  TACATGGATA  ATTTTATTTG  CAGCTGAAAC  TAAAGAGGAA  TTAATGCTAT   300
GCTACAAACA  ACTGGAAAAG  GCTGTGACTG  CAGCGGGATT  AATCAATCAT  AGCCCTGATA   360
AAATCCAAAC  TTCTACTCCC  TTTCAGTATT  TAGGAATGAA  AGCAGAATAA  AGTACTATCA   420
AGCTTCAAAA  GGTTCAAATT  AGAAGAGATG  ATTTAAAAAC  TCTAAATGGC  CGGCCTGCCT   480
TCCTTCCTTC  CCTCCCTCCC  TCCCTCCCTC  CCTCCCTTCC  TTCCTTCCTC  CCTCCCTCTC   540
TCTTTCGACG  GTCTCCCTCT  GTTGCCGAGG  CTGGACTGTA  CTGCCATGAT  C            591
```

(2) INFORMATION FOR SEQ ID NO:18:

(i) SEQUENCE CHARACTERISTICS:
        (A) LENGTH: 485 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
GATCACTTGA  GGCCAGGAGT  TCAAGACCAG  CCTGAGCAAC  CTAGTGAAAC  CCCGTTTCTA    60
CAAAAAATAA  AAATTTAAGA  AATAGCTGGA  TGCAGAGGCA  TCTGCCTGTA  GTCCCAGCTA   120
CCCAGGAGGT  TGAGGAAGGA  GAATCACTTG  AGCCCAGAAG  CTTGAGGTTG  TAGTAAGGAA   180
TGTTCATGCC  ACTGCACTGC  AACATGGGTG  ACAGTGCAAG  TTTCTGCCTC  AAAAGGAAGG   240
AAGGAAGGAA  GGAAGGAAGG  AAGGAAGGAA  GGAAGGAAGG  AAGGCAGGCA  AGAAGAAAAG   300
AAGGCAGGGA  GAGACGGAGG  GAAAGACAGA  AAGGAAAGAA  AACCTATAAA  AAAGTATAAT   360
CCTGTGAGTC  CACAGATGAG  ACAGAGAAAA  ATCTGGAAAG  GATTTTAAAA  TAAGTATGCT   420
TAAATTCTTC  AAAGAGACAT  AGAAAGGAAT  AGAACCCACA  AATAAGAAT   GGAAATATTC   480
GAAAA                                                                    485
```

(2) INFORMATION FOR SEQ ID NO:19:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
GATCTTATGA  CATTTTCCCA  GGACACCAAG  ATATAAAACC  CCAACCAACA  TTGCTACTGC    60
```

| TAAAGTAAAC | TTTTGCCTGG | CTTGCCAAGA | TTTTTGGCCA | AGAAATGAGA | TTTCCTGAGG | 120 |
| GTGGCATTCC | CTCTGCACTA | CCAAAGTCTC | CTTCTGAGAC | TTTTTGGTCA | GCTTATGAAG | 180 |
| CTTCTCAAGG | CAAGTGTCTG | GTTAGCATCT | CCCTCCCTCC | ACTCTGGAAA | TCTTAAAGCT | 240 |
| GAAAGAATGA | ATGAATGAAT | GGATGAATGA | ATGAATGAAT | GAGAAGACAG | AGAGAGAGAA | 300 |
| GGAAGGAAGG | AAGGAAGGAA | GGAAGGAAGG | AAGGAAGGAA | AGAAAGAAAA | GAAAGAAAG | 360 |
| AAGAGAGAAA | GAGAGAAAGA | AAGAAAGAGA | GAAAGAGAGA | GAGAGAGAGA | GAGAAAGAGA | 420 |
| GAGAGGAAGA | GAAGAAGTCC | TCTTAAAAAA | TAGCCTGAGA | AACTGGGCTA | TGTTGGCTTT | 480 |
| TTTTTTTTTC | TGTCAGTAGG | AAATATTTAT | TCAACCTCAC | TGCTAAAAAA | AAACCAAAAC | 540 |
| AAACAAACAA | AAAAACCTAA | TAATTTCAGG | AAAGCTGCTG | TTTCTCGTGT | TCTGATC | 597 |

(2) INFORMATION FOR SEQ ID NO:20:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

| GATCACGCCA | CTGCACTCCA | GCCTGGGTGA | CAGTGTGAGA | CCCTGTCAAG | GAACGAACGA | 60 |
| AGGAAGGAAG | GAAGGAAGGA | AGGAAGGAAG | GAAGGAAGGA | AGGAAGGAAG | GAAGGAAGGA | 120 |
| AGGAGGGAAG | GAAGGAAAGA | AGGCAGGCAG | GCAGGCAGGC | AGGAAGGAAG | GAAGGAAAGA | 180 |
| AGGAAGGAAG | GAAAGAAGGA | AGGAAGGAAA | GAAGGAAGGA | AGGTAGGAAG | GTAGGAAGGA | 240 |
| AGGAAGGAAG | GAAAGAAGGA | AGGAAGGAAG | GCAGTCAGGG | AGNAAGGAAG | GAAGGCAGGC | 300 |
| AGGCAGGCAG | GCAGGCAGGC | AGGCTTGCAA | ATGTAGTTAA | GTTAAAGATC | | 350 |

(2) INFORMATION FOR SEQ ID NO:21:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

| GATCATGCGG | GCAGCTTTGG | GGTATTTCAG | ACGGTGTGGG | GAGCATGGTC | TGAATGTGCC | 60 |
| TTGCTCCGGC | AGCAGCATGC | AGTAGTGGCA | GTGGTACTTA | GGGCATGTGA | GAGCACCCTG | 120 |
| CCTCTCCTAT | CCCTGACCCA | GCAGCATGCA | GTAGCGGCAG | TGGTACTTAG | GGCATGTGAG | 180 |
| AGCACCCAGC | CTCTCCTATC | CCTGACCCAG | CAGCTGGCAG | CAGCAGCAGC | AGCAGCAGCA | 240 |
| GCAGCAGCCG | CCTCAGGGCA | GGAGGCAGAG | CCTTCAGGCG | TGG | | 283 |

(2) INFORMATION FOR SEQ ID NO:22:

(i) SEQUENCE CHARACTERISTICS:
        (A) LENGTH: 494 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

-continued

| | | | | | | |
|---|---|---|---|---|---|---|
|GATCACTGCA|CTCCAGCCTG|GGTGACAGAA|TAAGACGAAA|GAGAGAAAGA|GAGAGGGAAA|60|
|GAAAGAAAGA|GAGAGAGAGA|GAGAGAGAGA|GAGAGAGAAA|GAAAGAAAGA|AAGAAAGAAA|120|
|GAAAGAAGAA|AGCAAGAAGG|AAGGAAGGAA|GGAAAGAAAG|CAGCAGAAAA|AGAGGAAGGG|180|
|AGGGAGGAAG|GAAGGAAGGA|GGAAGGGAG|GGAGGGAAGG|AAGGAAGGAA|GGAAGGAAGG|240|
|AAGGAAGGAA|GGAAGGAAGG|AAAGAGAGAG|AGAGAAAGAA|AATANNNNNN|NNNNNNAACT|300|
|CCNNNAAACC|CACAATTCAG|ACACACAGCT|CACACACAGG|TCTCCAGCAT|AGACATATTT|360|
|ATACATCCAT|TTACTCAAAC|ACTCACAATA|CAATCACATA|AAACAGGCAG|ACAGTTCACA|420|
|TGCCAACACA|CTCTTGCACA|GACACGCAAA|CAGAAGCATG|GAATTTGTAC|AGAGCACGCT|480|
|CACAGTGTCT|GATC| | | | |494|

( 2 ) INFORMATION FOR SEQ ID NO:23:

( i ) SEQUENCE CHARACTERISTICS:
        ( A ) LENGTH: 301 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

| | | | | | | |
|---|---|---|---|---|---|---|
|GATCGTGCCA|CTGTACCCCA|GCCTGGGCTA|CAGAGCGAGA|CTCCATCTCA|AAAAAAAAA|60|
|AGAAAGAAAG|AAAGAGAGAA|AGAGAGAGAG|AGAGATGAAA|GAAGAGAGA|GAGGGAAAGA|120|
|AAGGAAGGAA|GGAAGGAAGG|AAGGAAGGAA|GGAAGGAAGG|CAGGCAGGCA|GGCAGGCAGG|180|
|CAGGCAGGCA|GGCAGGCAGG|CGGACAGCAA|GAAGACACCG|TTTTGCCATG|AGGTTAGACA|240|
|CGCGGACAGG|CACAGAGCAG|ACGCACGTGC|ACCATGCTAT|CATGGCAGGA|CAGGTTCACA|300|
|T| | | | | |301|

( 2 ) INFORMATION FOR SEQ ID NO:24:

( i ) SEQUENCE CHARACTERISTICS:
        ( A ) LENGTH: 538 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

| | | | | | | |
|---|---|---|---|---|---|---|
|GATCATCAAA|ATACAATTAT|AGAAATATTT|ATAAGCAGCA|TTATTCATAA|TCGCCAAAAA|60|
|CTGGAAGCAG|TGCGATGGCA|AAATAGATGC|ATAAATGGTG|ATAAGTATAA|GAGGGAAGA|120|
|AAGAATGAAA|GAAAGAATGG|AAGGAAGGAA|GGAAGGAGGG|AAGGAAGGAA|GGAGGGAAGG|180|
|AAGGAGGGAA|GGAAGGAGGG|AAGGAGGGAA|GGAAGGAGGG|AAGGAAGGAA|GGGAGGAAGG|240|
|GAGGGAGGGA|GGGAGGGAGG|AAGGGAGGGA|GGGAGGGAGG|GAGGGAGGGA|AAGGACTAGA|300|
|GGGTGGAAGA|TAGGGAGAGA|AACAAGTAAA|TAAGCTAGCT|CTTTCCTAGA|AAATAATTTC|360|
|ACCAACGTTT|CTGTGACATT|CAAGAAAACA|ACTGGACTT|GGAAACAATT|AAAAATAAAT|420|
|AAACAAAGT|ATGCCACTAG|ACTCTAAAGT|CAGTGGTGTG|GGAAGCAGAG|GTTATCAGTG|480|
|TTCAGAGGAG|AGAAGACTCC|CACAGAATAG|GGCTGTCAGG|AATGAGCTCA|GGGAGGAA|538|

( 2 ) INFORMATION FOR SEQ ID NO:25:

( i ) SEQUENCE CHARACTERISTICS:
        ( A ) LENGTH: 421 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:25:

```
GATCACCTGA GGTCAGGAGT TTGAGACCAG CCTGGACAAC ATGACAAAAC CCCTATCTAA      60
AAAAAAAGAA ATAGCTAGGC ATGGTGGTGT GCACCTGTAG TCCCAGCTAC TTGGGAGGCT     120
GAGGCAGAGA ATCACTTGAA CCCGGGAGGC AGAGGTTGCA GTGAGCCGAG GAGGCGCCAC     180
TTCACTCCAG CCTCTGTCTC CAAAGAAAGA AAGGAAAAGA AAGAAGGGAA GAAAGAGAGA     240
GGGAGGAAAG AAGGGGAGGA AGGAAGGAAG GAAGGAAGGA AGGAAGGAAG GGAGGGAGGG     300
AGGGAGGGAG GGAGGGAGGG AGGGAGGGAG GGAGGGAAAA AGAAAGAGG TGAGCACACG      360
GTTACATTGA GGAAAACAAA GATGAAACTT CACATCACAT TCCAACAAGT CACAGCTTGA     420
T                                                                     421
```

(2) INFORMATION FOR SEQ ID NO:26:

(i) SEQUENCE CHARACTERISTICS:
(A) LENGTH: 446 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:26:

```
GATCTCAGGT GACCCACCAG CCTCAGCCTC CCAAAGTGCT GGGATTACAG GCCTGTGCCA      60
CTGCACCCAG CCATCTGTTC AGTACTTTCA TTATAAGAGA GAAGGAGGA GAGGGAAGGG      120
AAGGGAGGGA AGGGAGGGG AAGGAATCA ATGGGAAAGG AGGGTCAAGA AGGAGAAGGA       180
GAGAAGGAAG GAAGGGAGGG AGGAAGAGAG GAAGGAAGGA AGGAAAGAAG GAGGGAAGGA     240
AGGAAGGAAA GAAGGAGGGA AGGAAGGAAG GAGGGAGGAG GGAAGGAAGG AAGGAAGGAA     300
AGAAGGAAGG AAGGAAGGAA AGAGGGAAGA AAGGAAGGAA GGAAAGAAAG AAGGGAGGAA     360
GGGAGGGAGG GAGGGAGGGA ATGAGTGGNA GAAGCCAAGT CTGCAGTTGG GAAATCATGG     420
GACGTGCTGG CTTTTCCTCT CTGATC                                          446
```

(2) INFORMATION FOR SEQ ID NO:27:

(i) SEQUENCE CHARACTERISTICS:
(A) LENGTH: 287 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:27:

```
GATCACTTGA GCCCAGGAGT TCAAGGCTGT GGTAAACTAT AATCACACTA CTGCACTCCA      60
GCCTGGGTGA CAGAGAAAGA CCCTGTCTCA AAAAGGAAG GAAAGAAGGA AGGAAGGAAG      120
GAAGGAAGGA GGGAGGGAGG GAGGGAGGAA GGGAGGGAGG GAGGGAAGGA GGGAAGGAAG     180
GAAGGAAGGA AGGAAGGAAG GAAGGAAATA GCAGCTCTGA GCTTAGAAAA AGGAGTCTAT     240
TTCTAAGTGG GAGATGGGGA GAAGGAGGGA ACTGGGGAGG TGAGGAA                   287
```

(2) INFORMATION FOR SEQ ID NO:28:

(i) SEQUENCE CHARACTERISTICS:
(A) LENGTH: 252 base pairs (B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:28:

| | | | | | | |
|---|---|---|---|---|---|---|
| GATCATTAGG | TTGAAAAAGA | GCTAAAAGAT | GAAACCGATT | GGCACTGGTG | TGTGGTGGTG | 60 |
| GTGGAGGAGG | TGGTGGTGGC | GGCGGCGGTG | GTGGTGGTGG | TGGTGGTGGT | GGTGGCGGTG | 120 |
| GTGGTGGTAG | GAATTACTCA | AGTTACTGGA | AACATGCTGG | TATCTTTTTT | TAGTTTAGGT | 180 |
| AGTAAACCTG | GTAATGAACA | CTAAGTCAAA | CAACAAATAC | TAATTTCCAT | CTCATGCACA | 240 |
| AATGATATGA | AA | | | | | 252 |

(2) INFORMATION FOR SEQ ID NO:29:

(i) SEQUENCE CHARACTERISTICS:
(A) LENGTH: 329 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:29:

| | | | | | | |
|---|---|---|---|---|---|---|
| GATCAGACAC | TCTAAAGTCA | CATTCCTTTA | GAGGAACTGG | ACAATCAAAT | TTTGATGGTG | 60 |
| TTCTAATGGT | TTGTAAGGCA | ACAAAACACA | AAACTTTGTG | GTGGTGGTGG | TGGTGGTGGT | 120 |
| GGTGGTGGTG | GTGGTATCTT | CCATCACTTG | CCAAGGGCTT | AGCCTGGACC | TGCACACTCA | 180 |
| CTATCTCCTT | GACCATTTGC | ACCATCACCA | GGAGGGAGGC | ACTAGGTCCC | CCGTTCTCAC | 240 |
| TGTTATAAAT | AACAAACAGG | TCTCCAAGGG | GTGAGTAACT | TTCTCGTGGA | CACACAGAGG | 300 |
| CAGGTCTAGG | ATTTGAACCC | AGTTTGTCT | | | | 329 |

(2) INFORMATION FOR SEQ ID NO:30:

(i) SEQUENCE CHARACTERISTICS:
(A) LENGTH: 276 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:30:

| | | | | | | |
|---|---|---|---|---|---|---|
| GATCTCTCTA | GGTCCTATTC | TCTTTCAACC | CTCTAGGGAA | CTCAGGAAAC | ATTGGGCTAT | 60 |
| TGTCCATAAT | GTGGTGATGG | TGGTGGTGAT | GGTGGTGGTG | GTGGCGGTGA | TGGCAGCGGC | 120 |
| AGTGGTGATG | GCGATGGCGG | CAGCGGCGGT | GGTGGTGGTG | GTGTCACCCG | AGGCTGCCTT | 180 |
| GGTCCAGCCA | GCACGCAGCC | TTCTCTATTC | ATTCTCTCTT | GTGTGGACCC | GTGGGGAAT | 240 |
| TCTATGAGTC | TTGCCACTTC | ANGGCTCCAC | TCAGAA | | | 276 |

(2) INFORMATION FOR SEQ ID NO:31:

(i) SEQUENCE CHARACTERISTICS:
(A) LENGTH: 185 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:31:

| | | | | | | |
|---|---|---|---|---|---|---|
| GATCATAGAG | CAGGTCACCA | GGATGAAGAC | TGCATGAAGG | CAAGGGCTTT | GATGTACTCA | 60 |

| | | | | | |
|---|---|---|---|---|---|
| TTGTCCTGGC | CCCGGCATGG | AGGTGCTGGA | AGGCAAGAGG | GAGGAGGAGG | GAGGCAGAGA | 120
| TGGAAGGATG | AAGGAGAAGA | AGGAAGGAAG | GAAGGAAGGG | AAGGAGGGAG | GGACAGAGGG | 180
| AGGAT | | | | | | 185

( 2 ) INFORMATION FOR SEQ ID NO:32:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

GGAAAGTTTT TTTAAAAAGA TC          22

( 2 ) INFORMATION FOR SEQ ID NO:33:

( i ) SEQUENCE CHARACTERISTICS:
        ( A ) LENGTH: 140 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

| | | | | | |
|---|---|---|---|---|---|
| GATCTACATG | CATAGTTTAT | TTTTTATGTT | CTTTTATGTT | TGTTAATATG | TAAATATATT | 60
| TGTGATATAT | TATTAAGTNA | GAATATCAAC | NGCCTTCCTT | CTTTCCNNCC | CTCCCCACTT | 120
| CCCTNCCTTN | CCTTCCCAGC | | | | | 140

( 2 ) INFORMATION FOR SEQ ID NO:34:

( i ) SEQUENCE CHARACTERISTICS:
        ( A ) LENGTH: 211 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

| | | | | | |
|---|---|---|---|---|---|
| TCTGACAAGG | TCTGTCTCTG | TCACCTAGGC | TAGAATGCAG | TGGTGNAATC | AATAGCTCAC | 60
| TGCAGCCTTG | ACCTTATGGA | CTCAAGTAAT | CCTCCTACCT | CAGNNTCCNN | ACAGNNGGGA | 120
| CCTCAGGTGC | ATACCACGCT | CTGCTAATTT | ATAGAGATGG | AGTCTTACCA | TTTTGCCTAA | 180
| GATGGTCTCC | AACTCCCGGG | TTCAAGTGAT | C | | | 211

( 2 ) INFORMATION FOR SEQ ID NO:35:

( i ) SEQUENCE CHARACTERISTICS:
        ( A ) LENGTH: 374 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

| | | | | | |
|---|---|---|---|---|---|
| GATCTTGGCT | GGGTCAACAC | TCCTTCCTGG | GCTTCAGTTT | CTCATCTAAG | AAGAGAGAGT | 60
| TGGAGGATTG | TGGTGGGGGG | TTGGTCAGTG | AAGGTAGGCA | TCCCAGGGTG | GGTANCCATG | 120
| AGGGTCTCTC | TAGTCCTTTT | TTCTTCTTCA | CCCTTACACT | TATCCACCCA | TCCAACCATC | 180

```
CATCCATCCA  TCCATCCATC  CATCCATCCA  TCCATTTTTT  CTTTTTTCTT  TTTTTCTTTT        240

TTTGAGATGG  AGTCTTGCTC  TGTTGCCCAG  GCTGGAGTGC  AGTGGCATGA  TGTCAGCTCA        300

CTGCAACCTC  TGCCTCCTGA  GTTAGAGTGA  TTTTCCTGCC  TCAGCCTCCT  GAGTAGCTGG        360

GACTATAGGC  ACAC                                                              374
```

( 2 ) INFORMATION FOR SEQ ID NO:36:

( i ) SEQUENCE CHARACTERISTICS:
          ( A ) LENGTH: 106 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:36:

```
GATCACCTGA  GGGAGCTCAA  GACCAGCCTG  GCCAACATGA  TGAAACCCCG  TATATACTAA         60

AAAGTACAAA  AAATCANNNG  GGTGTGTGGT  GGGANTGTAA  TNTTAG                        106
```

( 2 ) INFORMATION FOR SEQ ID NO:37:

( i ) SEQUENCE CHARACTERISTICS:
          ( A ) LENGTH: 124 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:37:

```
GAAAGAAAGA  AAGAAAGAAA  GAAAGCAAGC  AAGCAAGCAA  GCAAGCAAGC  AAGCAAGCAG         60

GCAGGCAAGN  NAGCGGCGTC  ACGCCNGTAA  TCCCAGCACT  TTGGGAGGCC  GAGGCGGGCA        120

GATC                                                                          124
```

( 2 ) INFORMATION FOR SEQ ID NO:38:

( i ) SEQUENCE CHARACTERISTICS:
          ( A ) LENGTH: 213 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:38:

```
GATCATTTCC  CAGTACATAA  GGACCTGTTT  CTCTCCTGCT  AACATTAACC  CTACTTGAGA         60

CTTAGAGAAA  GAGGCATCAC  ACTTGAAAGT  CTCCTGTGGG  TATAATGTCT  ACTCTTTGTT        120

TCATGAAAGG  ATATCCTGGG  GTGGTAGCTT  TTTGGTTTTC  TTTCTCTCTT  TCTCTCTTTC        180

TTTCTTTCTT  TCTTTCTTTT  CTTTCTTTCT  TTC                                       213
```

( 2 ) INFORMATION FOR SEQ ID NO:39:

( i ) SEQUENCE CHARACTERISTICS:
          ( A ) LENGTH: 67 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:39:

```
TTCCTTCCNT  CTTTTTTGTG  GATGGAGTTC  TGCTCTGTCA  CCCTGGCTGG  AGCGCAGTGG         60
```

```
C A C G A T C                                                                                    6 7
```

( 2 ) INFORMATION FOR SEQ ID NO:40:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

```
GATCGCACAC  TGCACTCCAG  CCTGGCAACA  GAGGGAGACT  TCATCAGAGA  CAGAGAGAGA    6 0

CAGAAAGAGA  GAGAGATAGA  GAAAGGGAGG  GAGGGAG                                9 7
```

( 2 ) INFORMATION FOR SEQ ID NO:41:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

```
AAGGAAGGAA  AGAAGGAAGG  AAGGAAGGAA  GGAAAAAAGA  AAAGAGAAAA  AAAAAGGAGA    6 0

GAGGTTGAAA  AAAACAACTA  CCTTGTGGTC  AGATC                                 9 5
```

( 2 ) INFORMATION FOR SEQ ID NO:42:

( i ) SEQUENCE CHARACTERISTICS:
        ( A ) LENGTH: 278 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

```
GATCACTTAG  CCTGGGAGGT  TGAGGCTGCA  GTGAGTCATG  ATTTTGCCAC  TACTGCATTC    6 0

CAGCCTGAGT  GACAGAGCCA  ACCTGTCTTG  AAAGAAAGAA  AGAAAAGAAA  GAAGGAAAGA    1 2 0

AAGAAAGAAA  GAAAGAAAGA  GAGAAAGAAA  GAAAGAAGGA  AGAAAGGAA  GGGAAAGAAA     1 8 0

GAAAGGAGGG  AGGGAAGGAG  GGAGGGAGGG  AAGGAGGGAG  GGAGGGAGGG  AGTATAAGAT    2 4 0

GTATCCCCTT  AGCAAATGTT  TAAATACACA  GTATAGTT                              2 7 8
```

( 2 ) INFORMATION FOR SEQ ID NO:43:

( i ) SEQUENCE CHARACTERISTICS:
        ( A ) LENGTH: 204 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

```
GATCAAAACT  GAGAAGCGCA  AAGACAAAGA  GTGTGCTTGT  TGAATACCAA  GTTGTATAGG    6 0

CTGCAGAAGA  GGAAGTGGTG  GGACTGGAGT  CTAGAGAGTC  TTGAACACCA  GGTTTGGGAG    1 2 0

TCTGGAGTTC  ACTTGGTGAG  TAACAATCTC  TGGCAGAGGA  AGACTCCGTC  TCAAAGAAAG    1 8 0

AAAGAAAGAG  AGAGAGAGAG  AGAG                                              2 0 4
```

( 2 ) INFORMATION FOR SEQ ID NO:44:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

```
AAAGAAAGAA AGAAAGAAAG AAAGAAAGAA AGAAAGAGAG GAAAGAAAGA AAGAAAAGAA      60
AAAAAGGAAA GGAATGAAAG GGATC                                            85
```

( 2 ) INFORMATION FOR SEQ ID NO:45:

( i ) SEQUENCE CHARACTERISTICS:
        ( A ) LENGTH: 140 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

```
GATCATGCTA CTGCACTCCT GCCTGGACGA CAGATTGAGA CCCCATCTCG GAAGGAAGGA      60
AGGAAGGAAG GGAGGGAGGA AGGAAGGAAG GAAGGGAGGG AGGGAGGGAG GAAGGGAGGG     120
AGGGAGGGAG GGAGGAAAAC                                                 140
```

( 2 ) INFORMATION FOR SEQ ID NO:46:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

```
ATAGAAAGTA AGAAAGAAAG GAAACAATTG TGTGATGCAC AGCTTTGTGC AGTGAGGNTT      60
TTTTTGCCTC CAAGGTTTTG GGACAAGAAG GCACACAGAG AATTAAAGGA GTCCAGAGTT     120
ACTTGCTGTC CTGATATAGA TCCACTAGTT CTA                                  153
```

( 2 ) INFORMATION FOR SEQ ID NO:47:

( i ) SEQUENCE CHARACTERISTICS:
        ( A ) LENGTH: 278 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

```
GATCTTTTTG GCTTTTTGGC ATAACATGGC TGGCAGAGCT CAAATTGTTT TTATCAGCTT      60
AGTTACCTCT ACCCAGTAGA AATACAACTG CTGAAATTGT AATTAGGTCT TTTATATTCC     120
TCTCCTTCCT CCCTCCCTCC CTCCCTCCCT CCGTCCCTCC CTTCCTCCCT TCCTTCCTTC     180
CTTTCTTCCC TACCCCCCTC TCTTTCTTCT TTTTATTTCC TTGTTTATTT CTGTCTAGCA     240
CTAGATTTCA TGGGAGACAT AGACTAAGAT ATAAATTT                             278
```

( 2 ) INFORMATION FOR SEQ ID NO:48:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

GCGGTACCCG GGAAGCTTGG        20

( 2 ) INFORMATION FOR SEQ ID NO:49:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

GATCCCAAGC TTCCCGGGTA CCGC        24

( 2 ) INFORMATION FOR SEQ ID NO:50:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

ACAAGGACCT CGTGAATTAC AATC        24

( 2 ) INFORMATION FOR SEQ ID NO:51:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

ACAGGATTCA CTCACATATT CCTG        24

( 2 ) INFORMATION FOR SEQ ID NO:52:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

GCACACTGGA AGTGCAAGTA AC        22

( 2 ) INFORMATION FOR SEQ ID NO:53:

( i ) SEQUENCE CHARACTERISTICS:
        ( A ) LENGTH: 24 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:53:

AGCCATGGTA AGTCTTAATA TATG    24

( 2 ) INFORMATION FOR SEQ ID NO:54:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:54:

TCTTCTCATC TCTCAAGCAG    20

( 2 ) INFORMATION FOR SEQ ID NO:55:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:55:

AGTGAGACTC CATCAAA    17

( 2 ) INFORMATION FOR SEQ ID NO:56:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:56:

GATCCATCCA TCCTTCCTC    19

( 2 ) INFORMATION FOR SEQ ID NO:57:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:57:

GATCCTGCCA CTGCAATC    18

( 2 ) INFORMATION FOR SEQ ID NO:58:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:58:

CTTTTAGTGG GGTTACCTGG C                             21

( 2 ) INFORMATION FOR SEQ ID NO:59:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

CCTGAGTTAT CCCAGGAGCC                               20

( 2 ) INFORMATION FOR SEQ ID NO:60:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

CTAAAAATCT CACTTGATAC TTG                           23

( 2 ) INFORMATION FOR SEQ ID NO:61:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

AGCCCAACCG CTGCCTC                                  17

( 2 ) INFORMATION FOR SEQ ID NO:62:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

GAGTGAGACT CCATCTCAAC                               20

( 2 ) INFORMATION FOR SEQ ID NO:63:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

AGCTCTATCA GATTGGTTTG G                             21

( 2 ) INFORMATION FOR SEQ ID NO:64:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

GATCTCAATA AACATTGATA CTGG      24

( 2 ) INFORMATION FOR SEQ ID NO:65:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

CTGCATGAGC TAAAGCATAC TG      22

( 2 ) INFORMATION FOR SEQ ID NO:66:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:66:

CACCACGTCC CGCCTCTAAT      20

( 2 ) INFORMATION FOR SEQ ID NO:67:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

AGGTCTGGGT GACAGAACA      19

( 2 ) INFORMATION FOR SEQ ID NO:68:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

GACAGAGCGA GACTCTGTCT A      21

( 2 ) INFORMATION FOR SEQ ID NO:69:

( i ) SEQUENCE CHARACTERISTICS:
        ( A ) LENGTH: 22 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:69:

CCTAGCTCCC AGAACTTTCT CC 22

( 2 ) INFORMATION FOR SEQ ID NO:70:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:70:

AGGAACTGTG GCTACAATAT TG 22

( 2 ) INFORMATION FOR SEQ ID NO:71:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:71:

TGCGGATTAG CCTACTTCAT C 21

( 2 ) INFORMATION FOR SEQ ID NO:72:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:72:

TAGCCTGCTT ACCTTGAG 18

( 2 ) INFORMATION FOR SEQ ID NO:73:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:73:

GGAGGGGGTC ACTTTCTG 18

( 2 ) INFORMATION FOR SEQ ID NO:74:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:74:

TTGGGCCTAG AAGGGAACTG                                                                                        20

( 2 ) INFORMATION FOR SEQ ID NO:75:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:75:

TGACAAAGCC AGACCTTG                                                                                          18

( 2 ) INFORMATION FOR SEQ ID NO:76:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:76:

ATAAGAGAGT AAATTTCTGG TG                                                                                     22

( 2 ) INFORMATION FOR SEQ ID NO:77:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:77:

ACAGCAAGAC TCCACCAA                                                                                          18

( 2 ) INFORMATION FOR SEQ ID NO:78:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:78:

TGACTGCAGC GGGATTAATC                                                                                        20

( 2 ) INFORMATION FOR SEQ ID NO:79:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:79:

ATCATGGCAG TACAGTCC                                                                                          18

( 2 ) INFORMATION FOR SEQ ID NO:80:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:80:

GTGACAGTGC AAGTTTCTGC 20

( 2 ) INFORMATION FOR SEQ ID NO:81:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:81:

CCCTCCGTCT CTCCCTGC 18

( 2 ) INFORMATION FOR SEQ ID NO:82:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:82:

CTCCCTCCAC TCTGGAAATC 20

( 2 ) INFORMATION FOR SEQ ID NO:83:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:83:

CATAGCCCAG TTTCTCAGGC 20

( 2 ) INFORMATION FOR SEQ ID NO:84:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:84:

GATCTTTAAC TTAACTACAT TTGCAAG 27

( 2 ) INFORMATION FOR SEQ ID NO:85:

( i ) SEQUENCE CHARACTERISTICS:
        ( A ) LENGTH: 22 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:85:

ACAGTGTGAG ACCCTGTCAA GG 22

( 2 ) INFORMATION FOR SEQ ID NO:86:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:86:

TATCCCTGAC CCAGCAGCTG 20

( 2 ) INFORMATION FOR SEQ ID NO:87:

( i ) SEQUENCE CHARACTERISTICS:
       ( A ) LENGTH: 19 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:87:

CTGCCTCCTG CCCTGAGGC 19

( 2 ) INFORMATION FOR SEQ ID NO:88:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:88:

GGGTGACAGA ATAAGACG 18

( 2 ) INFORMATION FOR SEQ ID NO:89:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:89:

ATGTCTATGC TGGAGACCTG 20

( 2 ) INFORMATION FOR SEQ ID NO:90:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:90:

GATCGTGCCA CTGTACC                                                                                                                                17

( 2 ) INFORMATION FOR SEQ ID NO:91:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:91:

CGCGTGTCTA ACCTCATGGC                                                                                                                             20

( 2 ) INFORMATION FOR SEQ ID NO:92:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:92:

GTGCGATGGC AAAATAGATG                                                                                                                             20

( 2 ) INFORMATION FOR SEQ ID NO:93:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:93:

ATTTTCTAGG AAAGAGCTAG C                                                                                                                           21

( 2 ) INFORMATION FOR SEQ ID NO:94:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:94:

CTCCAGCCTC TGTCTCC                                                                                                                                17

( 2 ) INFORMATION FOR SEQ ID NO:95:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:95:

CTTGTTGGAA TGTGATGTGA AG                                                                                                                          22

( 2 ) INFORMATION FOR SEQ ID NO:96:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:96:

CAGCCATCTG TTCAGTACTT TC     22

( 2 ) INFORMATION FOR SEQ ID NO:97:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:97:

TGATTTCCCA ACTGCAGACT TG     22

( 2 ) INFORMATION FOR SEQ ID NO:98:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:98:

TCAAGGCTGT GGTAAACTAT AATC     24

( 2 ) INFORMATION FOR SEQ ID NO:99:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:99:

ATAGACTCCT TTTTCTAAGC TCAG     24

( 2 ) INFORMATION FOR SEQ ID NO:100:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:100:

AAAAAGAGCT AAAAGATGAA ACCG     24

( 2 ) INFORMATION FOR SEQ ID NO:101:

( i ) SEQUENCE CHARACTERISTICS:
        ( A ) LENGTH: 24 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:101:

TGTTTCCAGT AACTTGAGTA ATTC 24

( 2 ) INFORMATION FOR SEQ ID NO:102:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:102:

ATGGTTTGTA AGGCAACAAA ACAC 24

( 2 ) INFORMATION FOR SEQ ID NO:103:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:103:

GCCCTTGGCA AGTGATGGAA G 21

( 2 ) INFORMATION FOR SEQ ID NO:104:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:104:

TCAGGAAACA TTGGGCTATT GTCC 24

( 2 ) INFORMATION FOR SEQ ID NO:105:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:105:

AGTGGCAAGA CTCATAGAAT TCCC 24

( 2 ) INFORMATION FOR SEQ ID NO:106:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:106:

GCTTTGATGT ACTCATTGTC 20

( 2 ) INFORMATION FOR SEQ ID NO:107:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:107:

GATCTTTTTA AAAAACTTT CC 22

( 2 ) INFORMATION FOR SEQ ID NO:108:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:108:

ATGTTCTTTT ATGTTTGTTA ATATG 25

( 2 ) INFORMATION FOR SEQ ID NO:109:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:109:

TGACAGAGAC AGACCTTG 18

( 2 ) INFORMATION FOR SEQ ID NO:110:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:110:

CCATGAGGGT CTCTCTAGTC 20

( 2 ) INFORMATION FOR SEQ ID NO:111:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:111:

CAGTGAGCTG ACATCATG 18

( 2 ) INFORMATION FOR SEQ ID NO:112:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:112:

ACCTGAGGGA GCTCAAGAC                                                              19

( 2 ) INFORMATION FOR SEQ ID NO:113:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:113:

GATCTGCCCG CCTCGG                                                                    16

( 2 ) INFORMATION FOR SEQ ID NO:114:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:114:

TCATGAAAGG ATATCCTGGG                                                            20

( 2 ) INFORMATION FOR SEQ ID NO:115:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:115:

GAGCAGAACT CCATCCAC                                                             18

( 2 ) INFORMATION FOR SEQ ID NO:116:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:116:

AGAGGGAGAC TTCATCAG                                                             18

( 2 ) INFORMATION FOR SEQ ID NO:117:

( i ) SEQUENCE CHARACTERISTICS:
        ( A ) LENGTH: 21 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:117:

GATCTGACCA CAAGGTAGTT G            21

( 2 ) INFORMATION FOR SEQ ID NO:118:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:118:

GTCATGATTT TGCCACTACT G            21

( 2 ) INFORMATION FOR SEQ ID NO:119:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:119:

ACATTTGCTA AGGGGATACA TC            22

( 2 ) INFORMATION FOR SEQ ID NO:120:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:120:

TGAGTAACAA TCTCTGGCAG            20

( 2 ) INFORMATION FOR SEQ ID NO:121:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:121:

GATCCCTTTC ATTCCTTTCC            20

( 2 ) INFORMATION FOR SEQ ID NO:122:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:122:

GACAGATTGA GACCCCATC                                                                                                  19

( 2 ) INFORMATION FOR SEQ ID NO:123:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:123:

GCACAAAGCT GTGCATCAC                                                                                                   19

( 2 ) INFORMATION FOR SEQ ID NO:124:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:124:

TACCCAGTAG AAATACAACT GC                                                                                               22

( 2 ) INFORMATION FOR SEQ ID NO:125:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:125:

CATGAAATCT AGTGCTAGAC AG                                                                                               22